US012657711B2

(12) United States Patent
Takei et al.

(10) Patent No.: US 12,657,711 B2
(45) Date of Patent: Jun. 16, 2026

(54) MEDICAL IMAGE PROCESSING DEVICE, OPERATION METHOD TO DERIVE INDIRECT FINDINGS IN MEDICAL IMAGE SHOWING AT LEAST SHAPES AND PROPERTIES OF TISSUE OF A LESION, AND OPERATION PROGRAM OF MEDICAL IMAGE PROCESSING DEVICE

(71) Applicant: FUJIFILM Corporation, Tokyo (JP)

(72) Inventors: Mizuki Takei, Tokyo (JP); Aya Ogasawara, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 251 days.

(21) Appl. No.: 18/476,316

(22) Filed: Sep. 28, 2023

(65) Prior Publication Data

US 2024/0020838 A1 Jan. 18, 2024

Related U.S. Application Data

(63) Continuation of application No. PCT/JP2022/011823, filed on Mar. 16, 2022.

(30) Foreign Application Priority Data

Apr. 2, 2021 (JP) ................................. 2021-063573

(51) Int. Cl.
G06T 7/00 (2017.01)
A61B 6/02 (2006.01)
(Continued)

(52) U.S. Cl.
CPC .............. *G06T 7/0012* (2013.01); *A61B 6/02* (2013.01); *A61B 6/50* (2013.01); *G16H 30/40* (2018.01);
(Continued)

(58) Field of Classification Search
None
See application file for complete search history.

(56) References Cited

U.S. PATENT DOCUMENTS 10,776,919 B2 * 9/2020 Kuratomi ............... A61B 6/502
2018/0182481 A1 6/2018 Wakasugi et al.
(Continued)

FOREIGN PATENT DOCUMENTS

CN 110993095 4/2020
JP 2012061206 3/2012
(Continued)

OTHER PUBLICATIONS

"International Search Report (Form PCT/ISA/210) of PCT/JP2022/011823," mailed on May 31, 2022, with English translation thereof, pp. 1-5.
(Continued)

*Primary Examiner* — Haris Sabah
(74) *Attorney, Agent, or Firm* — JCIPRNET

(57) ABSTRACT

Provided are a medical image processing device, an operation method of the medical image processing device, and an operation program of the medical image processing device, which can contribute to find the lesion that is hardly depicted, by using a method based on the thought of the doctor. A CPU includes an image acquisition unit, a first derivation unit, and a second derivation unit. The image acquisition unit acquires a medical image. The first derivation unit analyzes the medical image to derive indirect finding information related to an indirect finding that represents at least one feature of a shape or a property of peripheral tissue of the lesion associated with an occurrence of the lesion. The second derivation unit derives lesion
(Continued)

presence probability information indicating a presence probability of the lesion based on the indirect finding information.

14 Claims, 25 Drawing Sheets

(51) Int. Cl.
| | |
|---|---|
| *A61B 6/50* | (2024.01) |
| *G16H 30/40* | (2018.01) |
| *G16H 50/20* | (2018.01) |
| *G06F 3/04842* | (2022.01) |

(52) U.S. Cl.
CPC ......... *G16H 50/20* (2018.01); *G06F 3/04842* (2013.01); *G06T 2207/10081* (2013.01); *G06T 2207/20076* (2013.01); *G06T 2207/30096* (2013.01)

(56) References Cited

U.S. PATENT DOCUMENTS

| | | | | |
|---|---|---|---|---|
| 2018/0322633 A1* | 11/2018 | Kuratomi | ............... | A61B 6/502 |
| 2018/0365834 A1* | 12/2018 | Li | ............................ | G06N 3/08 |
| 2019/0295711 A1 | 9/2019 | Wakasugi et al. | | |
| 2021/0279920 A1* | 9/2021 | Kanada | ................. | G06V 10/82 |

FOREIGN PATENT DOCUMENTS

| | | |
|---|---|---|
| JP | 2014064703 | 4/2014 |
| JP | 2018102916 | 7/2018 |

OTHER PUBLICATIONS

"Written Opinion of the International Searching Authority (Form PCT/ISA/237) of PCT/JP2022/011823," mailed on May 31, 2022, with English translation thereof, pp. 1-8.

Tae Won Choi et al., "Comparison of Multidetector CT and Gadobutrol-Enhanced MR Imaging for Evaluation of Small, Solid Pancreatic Lesions", Korean Journal of Radiology, Jun. 2016, pp. 509-521.

Arya Haj-Mirzaian et al., "Pitfalls in the MDCT of pancreatic cancer: strategies for minimizing errors", Abdominal Radiology, Jan. 2020, pp. 457-478.

Konstantin Dmitriev et al., "Visual Analytics of a Computer-Aided Diagnosis System for Pancreatic Lesions", IEEE Transactions on Visualization and Computer Graphics, Mar. 2021, pp. 2174-2185.

"Search Report of Europe Counterpart Application", issued on Aug. 26, 2024, pp. 1-9.

"Notice of Reasons for Refusal of Japan Counterpart Application", issued on Sep. 2, 2025, with English translation thereof, pp. 1-6.

* cited by examiner

| CONTRIBUTION INFORMATION | |
| --- | --- |
| INDIRECT FINDING INFORMATION | CONTRIBUTION |
| PRESENCE PROBABILITY (ATROPHY) | 0.01 |
| PRESENCE PROBABILITY (SWELLING) | 0.06 |
| ⋮ | ⋮ |
| POSITIONAL INFORMATION (STENOSIS) | 0.18 |
| POSITIONAL INFORMATION (DILATION) | 0.42 |
| ⋮ | ⋮ |
| AREA RATIO (SWELLING) | 0.07 |
| AREA RATIO (STENOSIS) | 0.22 |
| ⋮ | ⋮ |
| CONCENTRATION REPRESENTATIVE VALUE (CALCIFICATION) | 0.18 |
| DEGREE OF MALIGNANCY | 0.28 |

PANCREATIC CANCER CAD

PATIENT: FUJI TARO  IMAGING DATE AND TIME: 03.14.2021 14:08  CONTRAST: NONE

ANALYSIS

FIG. 15

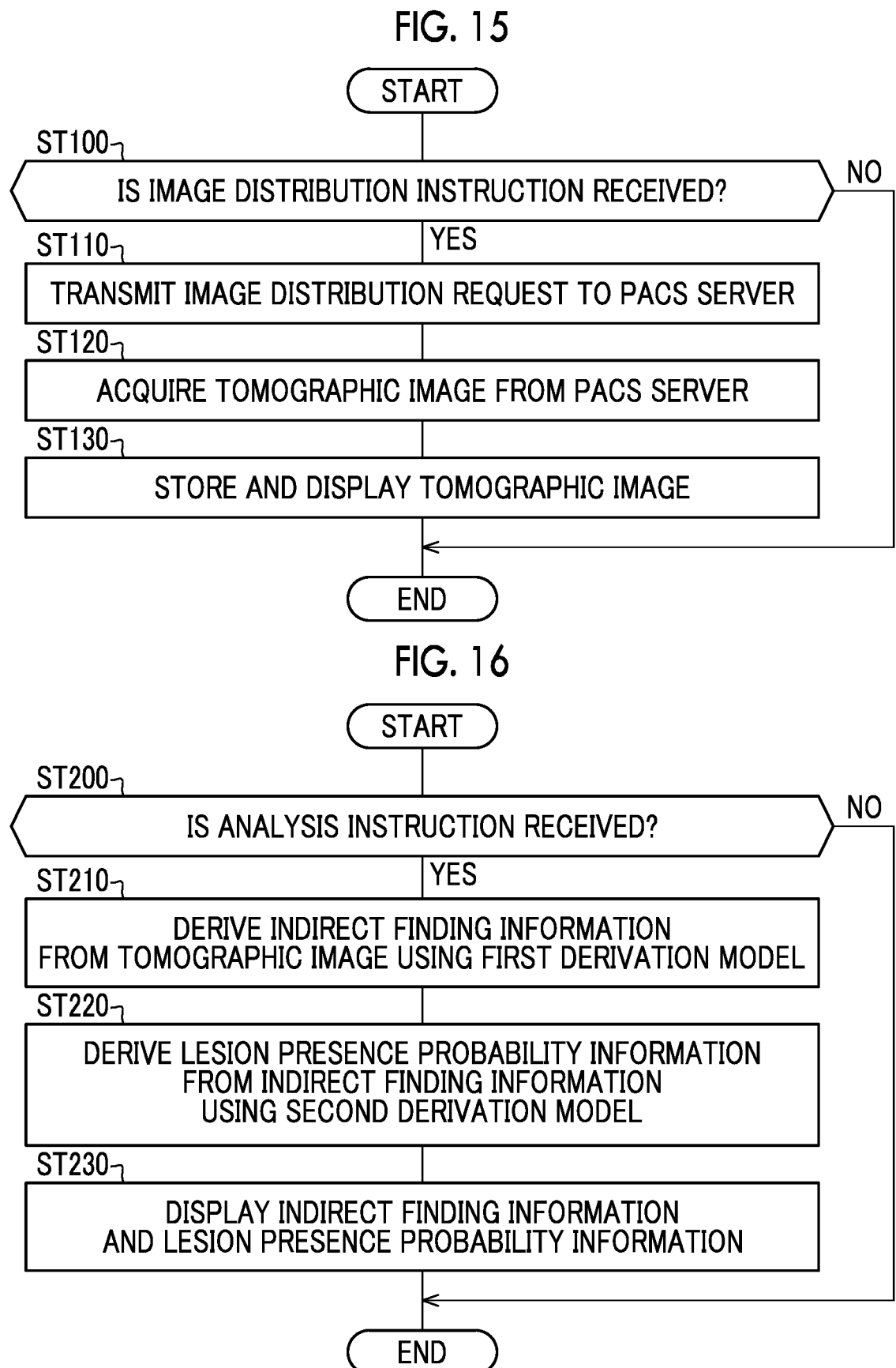

START

ST100 ─┐

IS IMAGE DISTRIBUTION INSTRUCTION RECEIVED?                    NO

YES

ST110 ─┐

TRANSMIT IMAGE DISTRIBUTION REQUEST TO PACS SERVER

ST120 ─┐

ACQUIRE TOMOGRAPHIC IMAGE FROM PACS SERVER

ST130 ─┐

STORE AND DISPLAY TOMOGRAPHIC IMAGE

END

FIG. 16

START

ST200 ─┐

IS ANALYSIS INSTRUCTION RECEIVED?                    NO

YES

ST210 ─┐

DERIVE INDIRECT FINDING INFORMATION
FROM TOMOGRAPHIC IMAGE USING FIRST DERIVATION MODEL

ST220 ─┐

DERIVE LESION PRESENCE PROBABILITY INFORMATION
FROM INDIRECT FINDING INFORMATION
USING SECOND DERIVATION MODEL

ST230 ─┐

DISPLAY INDIRECT FINDING INFORMATION
AND LESION PRESENCE PROBABILITY INFORMATION

END

| CONTRIBUTION INFORMATION | |
|---|---|
| TYPE | CONTRIBUTION |
| PRESENCE PROBABILITY (ATROPHY) | 0.01 |
| PRESENCE PROBABILITY (SWELLING) | 0.06 |
| ⋮ | |
| PROVISIONAL TUMOR PRESENCE PROBABILITY | 0.16 |
| ⋮ | |
| POSITIONAL INFORMATION (STENOSIS) | 0.18 |
| POSITIONAL INFORMATION (DILATION) | 0.42 |
| ⋮ | |
| PROVISIONAL TUMOR POSITIONAL INFORMATION | 0.25 |
| ⋮ | |
| AREA RATIO (SWELLING) | 0.07 |
| AREA RATIO (STENOSIS) | 0.22 |
| ⋮ | |
| PROVISIONAL TUMOR AREA RATIO | 0.13 |
| ⋮ | |
| CONCENTRATION REPRESENTATIVE VALUE (CALCIFICATION) | 0.18 |
| PROVISIONAL TUMOR CONCENTRATION REPRESENTATIVE VALUE | 0.17 |
| DEGREE OF MALIGNANCY | 0.28 |
| PROVISIONAL DEGREE OF MALIGNANCY | 0.42 |

| INDIRECT FINDING | PRESENCE PROBABILITY | AREA RATIO | CONCENTRATION REPRESENTATIVE VALUE |
|---|---|---|---|
| ATROPHY | 72% | 14% | |
| SWELLING | 38% | 8% | |
| STENOSIS | 10% | 3% | |
| DILATION | 82% | 22% | |
| FAT REPLACEMENT | 46% | | 956 |
| CALCIFICATION | 54% | | 982 |
| TUMOR (PROVISIONAL) | 76% | 26% | 889 |

MEDICAL IMAGE PROCESSING DEVICE, OPERATION METHOD TO DERIVE INDIRECT FINDINGS IN MEDICAL IMAGE SHOWING AT LEAST SHAPES AND PROPERTIES OF TISSUE OF A LESION, AND OPERATION PROGRAM OF MEDICAL IMAGE PROCESSING DEVICE

CROSS-REFERENCE TO RELATED APPLICATIONS

This application is a continuation application of International Application No. PCT/JP2022/011823 filed on Mar. 16, 2022, the disclosure of which is incorporated herein by reference in its entirety. Further, this application claims priority from Japanese Patent Application No. 2021-063573 filed on Apr. 2, 2021, the disclosure of which is incorporated herein by reference in its entirety.

BACKGROUND

1. Technical Field

A technology of the present disclosure relates to a medical image processing device, an operation method of the medical image processing device, and an operation program of the medical image processing device.

2. Description of the Related Art

In the medical field, computer-aided diagnosis (CAD), in which the presence probability, positional information, and the like of a lesion are derived by analyzing a medical image and presented to a doctor such as an image interpretation doctor, is put into practical use. For example, JP2018-102916A discloses the technology of calculating the presence probability of the lesion related to lung cancer such as a honeycomb lung or a ground-glass opacity by analyzing a tomographic image of the chest part imaged by a computed tomography (CT) device, and presenting the presence probability to a doctor with the probability image as the pixel value.

SUMMARY

In some cases, the lesion is not clearly depicted on the medical image depending on a type and a size of the lesion or a method of capturing the medical image. For example, a tumor related to pancreatic cancer is relatively clearly depicted in a contrast tomographic image of an abdomen, but the tumor related to the pancreatic cancer is hardly depicted in a non-contrast tomographic image.

In some cases, the doctor finds such a hardly depicted lesion by using an indirect finding shown in the medical image as a clue. The indirect finding represents at least one feature of a shape or a property of peripheral tissue of the lesion, which appears with the occurrence of the lesion. Examples of the indirect finding include atrophy, swelling, and calcification.

Since the CAD in the related art is developed on the premise that the lesion is clearly depicted on the medical image to some extent, it is difficult to find the lesion that is hardly depicted as described above. For this reason, there is a demand for the development of the CAD based on the above-described thought of the doctor, that is, finding the lesion that is hardly depicted by using the indirect finding as a clue.

An embodiment according to the technology of the present disclosure provides a medical image processing device, an operation method of the medical image processing device, and an operation program of the medical image processing device, which can contribute to find the lesion that is hardly depicted, by using a method based on the thought of the doctor.

Ag medical image processing device of the present disclosure comprises a processor, and a memory connected to or built in the processor, in which the processor is configured to acquire a medical image, derive indirect finding information related to an indirect finding that represents at least one feature of a shape or a property of peripheral tissue of a lesion associated with an occurrence of the lesion by analyzing the medical image, and derive lesion presence probability information that indicates a presence probability of the lesion based on the indirect finding information.

It is preferable that the indirect finding information is at least one of a presence probability of the indirect finding, positional information of the indirect finding, a shape feature amount of the indirect finding, a property feature amount of the indirect finding, or a degree of malignancy of the lesion based on the indirect finding.

It is preferable that the lesion presence probability information is at least one of a presence probability of the lesion or positional information of the lesion.

It is preferable that the processor is configured to present the lesion presence probability information.

It is preferable that the processor is configured to present the indirect finding information.

It is preferable that the processor is configured to present the indirect finding information having a relatively high contribution to the derivation of the lesion presence probability information as distinguished from the indirect finding information having a relatively low contribution.

It is preferable that the processor is configured to derive provisional lesion presence probability information that indicates a provisional presence probability of the lesion, which represents at least one feature of a shape or a property of the lesion, by analyzing the medical image, and derive the lesion presence probability information based on the indirect finding information and the provisional lesion presence probability information.

It is preferable that the provisional lesion presence probability information is at least one of a provisional presence probability of the lesion, provisional positional information of the lesion, a provisional shape feature amount of the lesion, a provisional property feature amount of the lesion, or a provisional degree of malignancy of the lesion.

It is preferable that the processor is configured to present the indirect finding information and the provisional lesion presence probability information.

It is preferable that the processor is configured to present the indirect finding information and the provisional lesion presence probability information, which have a relatively high contribution to the derivation of the lesion presence probability information as distinguished from the indirect finding information and the provisional lesion presence probability information, which have a relatively low contribution.

It is preferable that the lesion includes at least one of a tumor or a cyst.

It is preferable that the indirect finding that represents the feature of the shape includes at least one of atrophy, swelling, stenosis, or dilation, and the indirect finding that represents the feature of the property includes at least one of fat replacement or calcification.

It is preferable that the medical image is a non-contrast tomographic image of an abdomen in which a pancreas is shown and is used for diagnosing pancreatic cancer.

An operation method of a medical image processing device of the present disclosure comprises acquiring a medical image, deriving indirect finding information related to an indirect finding that represents at least one feature of a shape or a property of peripheral tissue of a lesion associated with an occurrence of the lesion by analyzing the medical image, and deriving lesion presence probability information that indicates a presence probability of the lesion based on the indirect finding information.

An operation program of a medical image processing device of the present disclosure for causing a computer to execute a process comprises acquiring a medical image, deriving indirect finding information related to an indirect finding that represents at least one feature of a shape or a property of peripheral tissue of a lesion associated with an occurrence of the lesion by analyzing the medical image, and deriving lesion presence probability information that indicates a presence probability of the lesion based on the indirect finding information.

According to the technology of the present disclosure, it is possible to provide a medical image processing device, an operation method of the medical image processing device, and an operation program of the medical image processing device, which can contribute to find the lesion that is hardly depicted, by using a method based on the thought of the doctor.

BRIEF DESCRIPTION OF THE DRAWINGS

Exemplary embodiments according to the technique of the present disclosure will be described in detail based on the following figures, wherein:

FIG. 10 is a diagram illustrating processing by a cutout image generation unit and a degree-of-malignancy derivation model;

FIG. 12 is a diagram illustrating contribution information;

FIG. 15 is a flowchart illustrating a processing procedure of the doctor terminal;

FIG. 16 is a flowchart illustrating a processing procedure of the doctor terminal;

FIG. 18 is a diagram illustrating a processing unit of a second embodiment;

FIG. 23 is a diagram illustrating processing by a second derivation model of the second embodiment;

FIG. 24 is a diagram illustrating contribution information of the second embodiment;

DETAILED DESCRIPTION

First Embodiment

Figure 1:
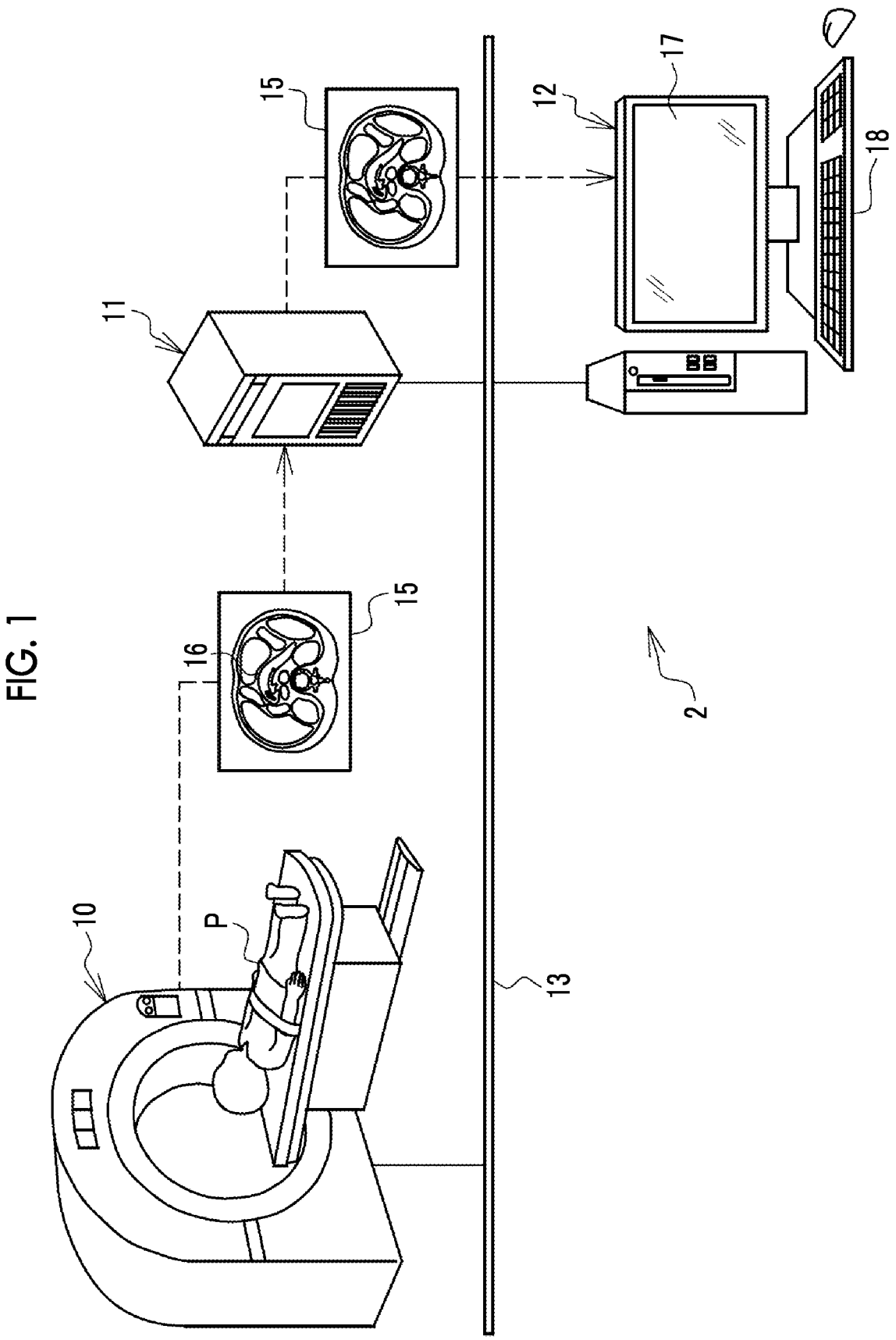
FIG. 1 is a diagram illustrating a medical system.

As an example, as illustrated in FIG. 1, a medical system 2 comprises a CT device 10, a picture archiving and communication system (PACS) server 11, and a doctor terminal 12. The CT device 10, the PACS server 11, and the doctor terminal 12 are connected to a local area network (LAN) 13 installed in a medical facility, and can communicate with each other via the LAN 13.

As is well known, the CT device 10 performs radiography on a patient P at different projection angles to acquire a plurality of pieces of projection data, and reconstructs the acquired plurality of pieces of projection data to output a tomographic image 15 of the patient P. The tomographic image 15 is voxel data that represents a three-dimensional shape of an internal structure of the patient P. In this example, a patient P, who is suspected to have pancreatic cancer is a target of imaging. Therefore, the tomographic image 15 is an image showing the abdomen of the patient P, mainly a pancreas 16. In addition, in this example, the tomographic image 15 is a non-contrast image captured without using a contrast agent. The tomographic image 15 is an example of a "medical image" and a "non-contrast tomographic image of the abdomen" according to the technology of the present disclosure. FIG. 1 illustrates a tomographic image 15 of an axial cross section.

The CT device 10 transmits the tomographic image 15 to the PACS server 11. The PACS server 11 stores and manages the tomographic image 15 from the CT device 10. The reconstruction of the projection data may be performed by the PACS server 11 or the doctor terminal 12 instead of the CT device 10.

The doctor terminal 12 is, for example, a desktop personal computer and is operated by the doctor. The doctor terminal 12 is an example of a "medical image processing device" according to the technology of the present disclosure.

The doctor terminal 12 comprises a display 17 and an input device 18. The input device 18 is, for example, a keyboard, a mouse, a touch panel, or a microphone. The tomographic image 15 is distributed to the doctor terminal 12 from the PACS server 11. The doctor terminal 12 displays the tomographic image 15 distributed from the PACS server 11 on the display 17. The doctor observes the pancreas 16 of the patient P shown in the tomographic image 15 to diagnose the pancreatic cancer. In FIG. 1, only one CT device 10 and one doctor terminal 12 are illustrated, but a plurality of CT devices 10 and a plurality of doctor terminals 12 may be provided.

Figure 2:
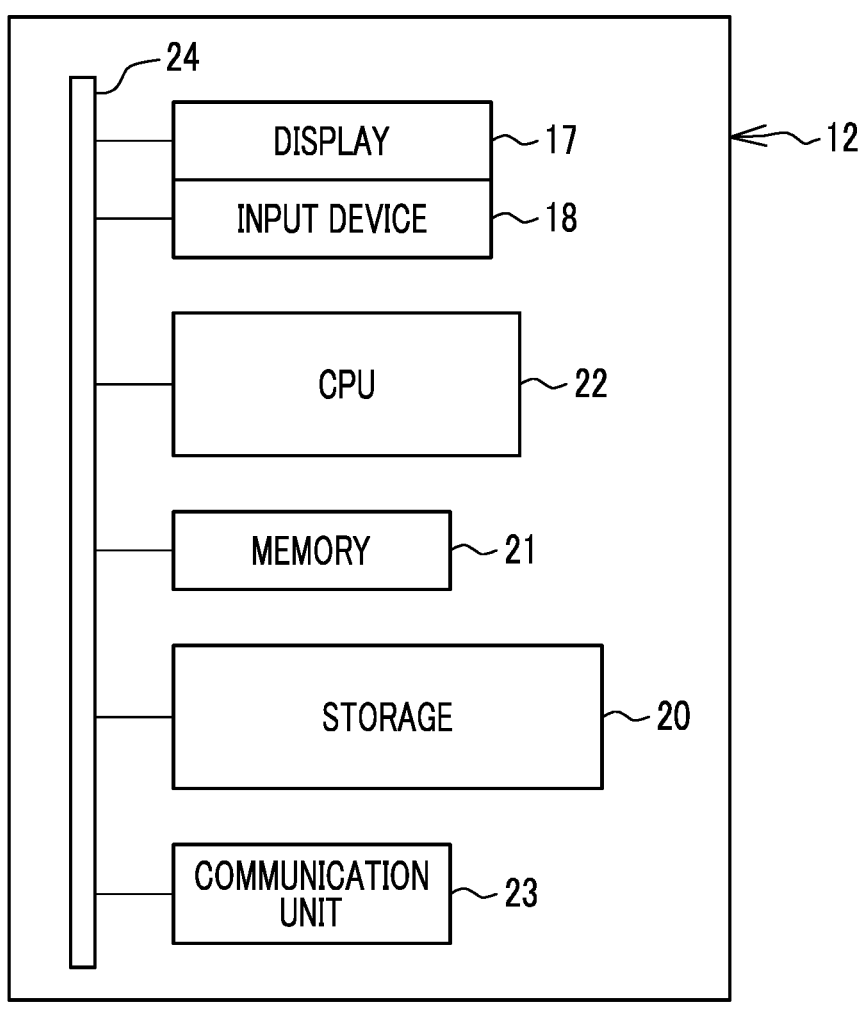
FIG. 2 is a block diagram illustrating a computer constituting a doctor terminal.

As an example, as illustrated in FIG. 2, the computer constituting the doctor terminal 12 comprises a storage 20, a memory 21, a central processing unit (CPU) 22, and a communication unit 23, in addition to the display 17 and the input device 18. These components are connected to each other via a busline 24.

The storage 20 is a hard disk drive that is built in the computer constituting the doctor terminal 12 or is connected to the computer through a cable or a network. Alternatively, the storage 20 is a disk array in which a plurality of hard disk drives are continuously mounted. The storage 20 stores a control program such as an operating system, various types of application programs, and various types of data associated with these programs. A solid state drive may be used instead of the hard disk drive.

The memory 21 is a work memory that is used to execute processing by the CPU 22. The CPU 22 loads the program stored in the storage 20 to the memory 21, and executes processing in accordance with the program. Thus, the CPU 22 collectively controls each unit of the computer. The CPU 22 is an example of a "processor" according to the technology of the present disclosure. The communication unit 23 controls transmission of various types of information with an external device such as the PACS server 11. The memory 21 may be built in the CPU 22.

Figure 3:
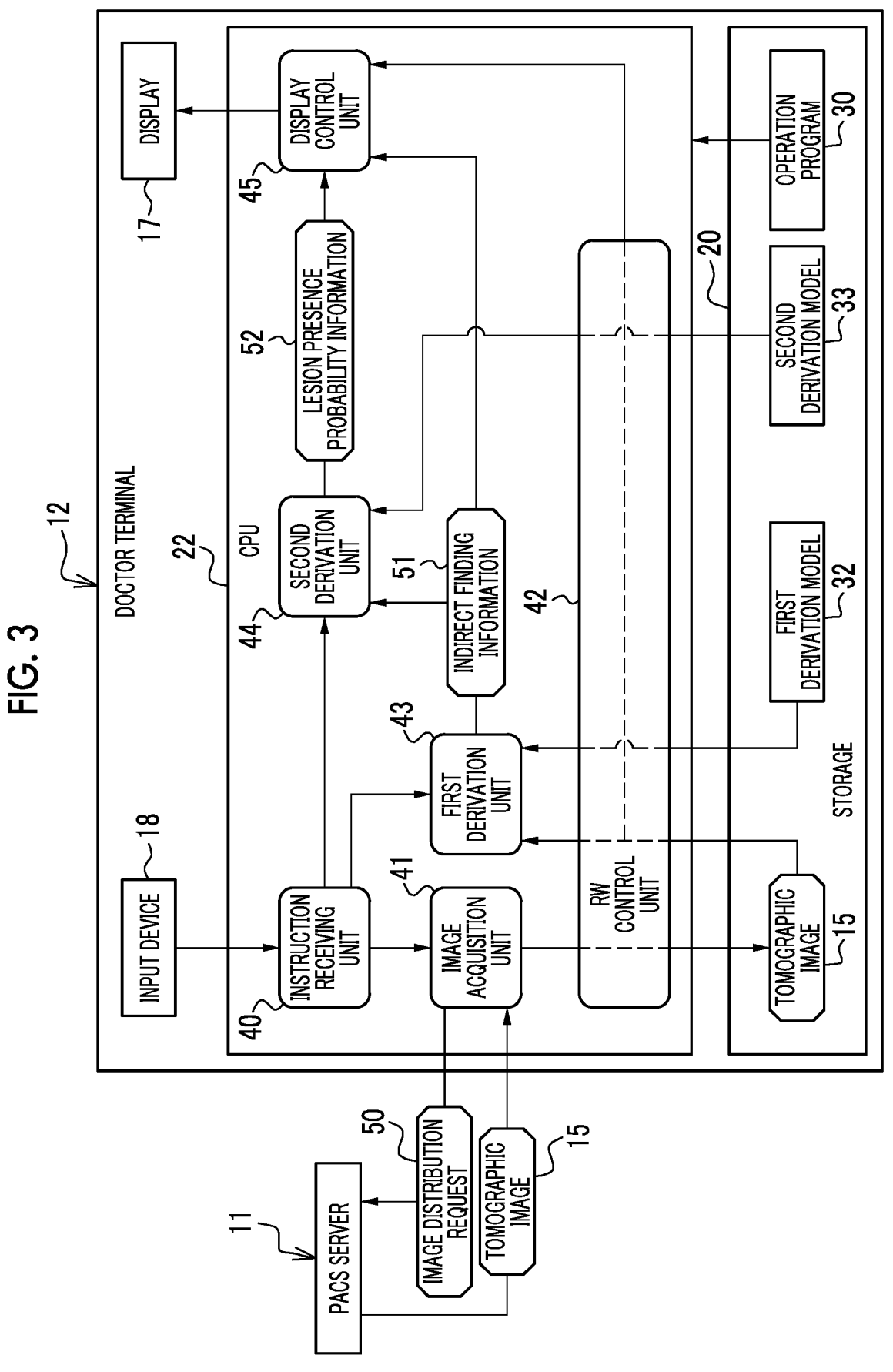
FIG. 3 is a block diagram illustrating a processing unit of a CPU of the doctor terminal.

As an example, as illustrated in FIG. 3, an operation program 30 is stored in the storage 20 of the doctor terminal 12. The operation program 30 is an application program that causes the computer constituting the doctor terminal 12 to function as a "medical image processing device" according to the technology of the present disclosure. That is, the operation program 30 is an example of an "operation program of a medical image processing device" according to the technology of the present disclosure. The operation program 30 may be recorded and distributed on an external recording medium, which is not illustrated in the drawing, and may be installed by the CPU 22 from the recording medium. Alternatively, the operation program 30 may be stored in a server or the like connected to a network in a state of being accessible from the outside, downloaded to the storage 20 by the CPU 22 in response to a request, and installed and executed. The tomographic image 15, a first derivation model 32, and a second derivation model 33 are also stored in the storage 20. The first derivation model 32 and the second derivation model 33 are machine learning models. In addition, the storage 20 stores data of various types of screens to be displayed on the display 17. In FIG. 3, only one tomographic image 15 is stored in the storage 20, but a plurality of tomographic images 15 may be stored in the storage 20.

In a case in which the operation program 30 is activated, the CPU 22 of the computer constituting the doctor terminal 12 cooperates with the memory 21 and the like to function as an instruction receiving unit 40, an image acquisition unit 41, a read/write (hereinafter, abbreviated as RW) control unit 42, a first derivation unit 43, a second derivation unit 44, and a display control unit 45.

The instruction receiving unit 40 receives various types of operation instructions from the input device 18. The operation instructions include an image distribution instruction instructing the PACS server 11 to distribute the tomographic image 15 of the patient P that is a diagnosis target, an analysis instruction of the tomographic image 15, and the like. The image distribution instruction includes a search keyword such as a patient identification data (ID) of the patient P that is a diagnosis target or an imaging date and time. The instruction receiving unit 40 outputs the search keyword of the image distribution instruction to the image acquisition unit 41. In addition, the instruction receiving unit 40 outputs the reception of the analysis instruction of the tomographic image 15 the first derivation unit 43 and the second derivation unit 44.

The image acquisition unit 41 transmits an image distribution request 50, which is a copy of the search keyword of the image distribution instruction from the instruction receiving unit 40, to the PACS server 11. The PACS server 11 searches for the tomographic image 15 requested by the image distribution request 50. The PACS server 11 distributes the searched tomographic image 15 to the image acquisition unit 41. The image acquisition unit 41 acquires the tomographic image 15 distributed from the PACS server 11. The image acquisition unit 41 outputs the acquired tomographic image 15 to a RW control unit 42.

The RW control unit 42 controls storage of various types of data in the storage 20 and reading out of various types of data in the storage 20. For example, the RW control unit 42 stores the tomographic image 15 from the image acquisition unit 41 in the storage 20. In addition, the RW control unit 42 reads out the tomographic image 15 from the storage 20, and outputs the read tomographic image 15 to the first derivation unit 43 and the display control unit 45.

The RW control unit 42 reads out the first derivation model 32 from the storage 20, and outputs the read first derivation model 32 to the first derivation unit 43. In addition, the RW control unit 42 reads out the second derivation model 33 from the storage 20, and outputs the read second derivation model 33 to the second derivation unit 44.

The first derivation unit 43 operates in a case in which the instruction receiving unit 40 receives the analysis instruction of the tomographic image 15. The first derivation unit 43 derives indirect finding information 51 by analyzing the tomographic image 15 using the first derivation model 32. The indirect finding information 51 is information related to indirect finding that represents at least one feature of the shape or the property of the peripheral tissue of the tumor associated with the occurrence of the tumor in the pancreas 16. The first derivation unit 43 outputs the derived indirect finding information 51 to the second derivation unit 44 and the display control unit 45. The "indirect" of the indirect finding is an expression in a sense that contrasts with a case in which the lesion, such as a tumor, is expressed as a "direct" finding that is directly connected to the disease, such as the cancer.

Similar to the first derivation unit 43, the second derivation unit 44 operates in a case in which the instruction receiving unit 40 receives the analysis instruction of the tomographic image 15. The second derivation unit 44 uses the second derivation model 33 to derive lesion presence probability information 52 based on the indirect finding information 51. The lesion presence probability information 52 is information that indicates the presence probability of a tumor in the pancreas 16. The second derivation unit 44 outputs the derived lesion presence probability information 52 to the display control unit 45.

The display control unit 45 controls display of various types of screens on the display 17. The various types of screens include a first screen 110 (refer to FIG. 13) that gives an analysis instruction of the tomographic image 15, a second screen 115 (refer to FIG. 14) that displays the lesion presence probability information 52 and the like.

The indirect finding that represents features of the shape of the peripheral tissue of the tumor (hereinafter, referred to as a shape indirect finding) include partial atrophy and swelling of the tissue of the pancreas 16 and stenosis and dilation of the pancreatic duct 16D (refer to FIG. 13 and the like). The indirect finding that represents features of the property of the peripheral tissue of the tumor (hereinafter, referred to as a property indirect finding) include fat replacement of the tissue (pancreatic parenchyma) of the pancreas 16 and calcification of the tissue of the pancreas 16.

Figure 4:
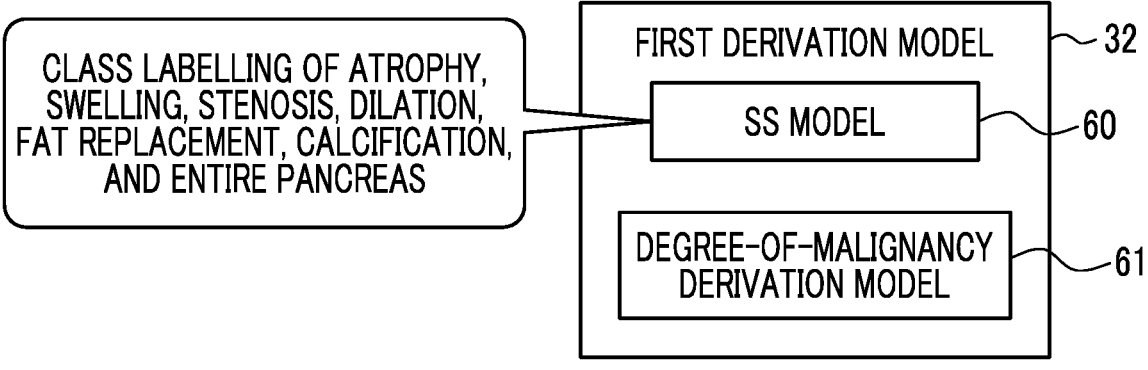
FIG. 4 is a diagram illustrating a first derivation model.

As an example, as illustrated in FIG. 4, the first derivation model 32 includes a semantic segmentation model (hereinafter, abbreviated as SS model) 60 and a degree-of-malignancy derivation model 61. As is well known, the SS model 60 is a machine learning model that outputs an output image in which a label representing an extraction object (class) is assigned to each pixel of the input image. In this example, the input image is the tomographic image 15, and the extraction object is a total of seven classes, which include each part of the pancreas 16 illustrating atrophy, swelling, stenosis, dilation, fat replacement, and calcification of the above-mentioned indirect findings, and the entire pancreas 16. The SS model 60 is constructed by a convolutional neural network (CNN) such as residual networks (ResNet) or U-shaped networks (U-Net). The SS model 60 actually includes an SS model that labels portions illustrating each indirect finding and an SS model that labels the entire pancreas 16, but here, in order to simplify the description, one SS model 60 is used.

Figure 5:
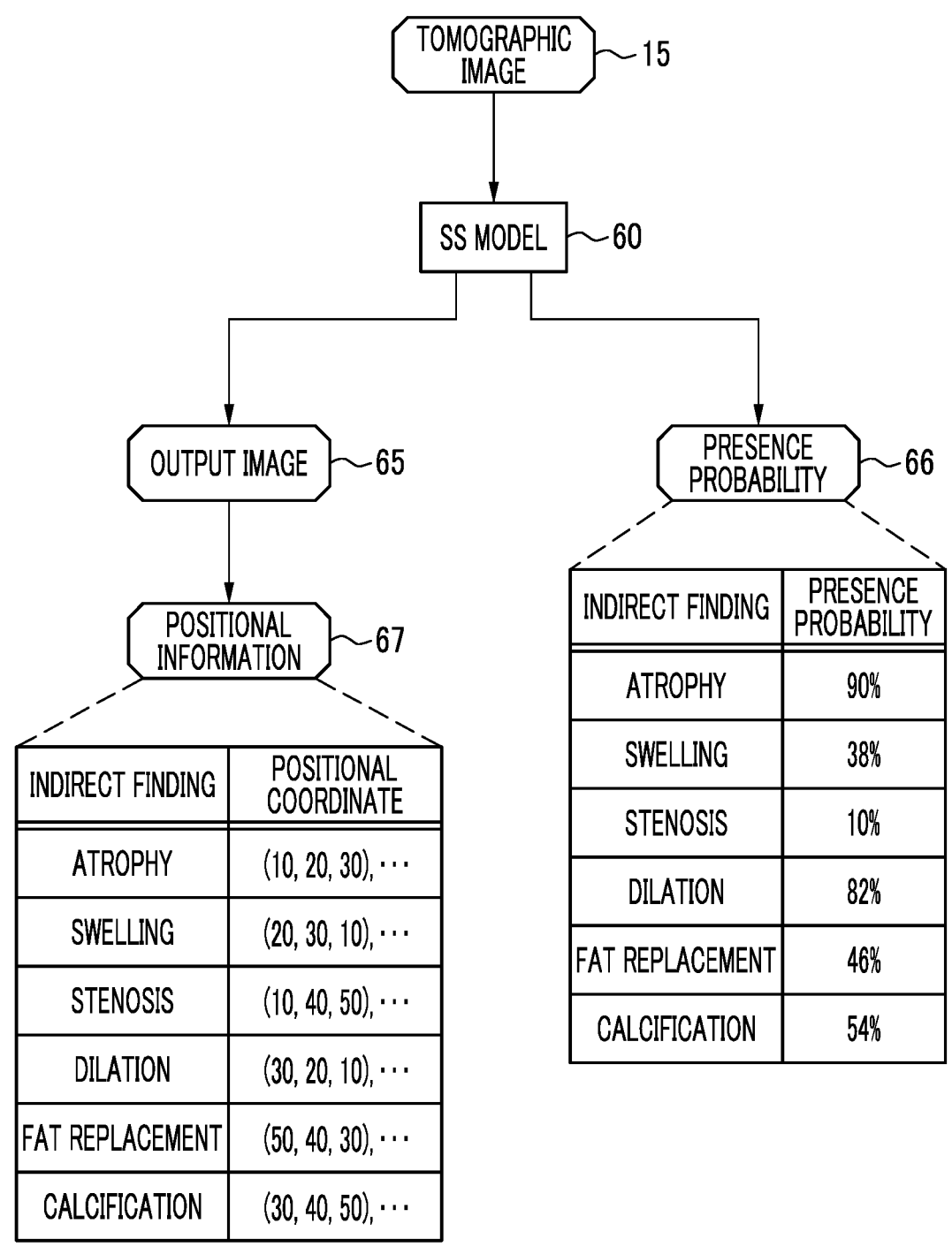
FIG. 5 is a diagram illustrating processing by an SS model.

As an example, as illustrated in FIG. 5, the first derivation unit 43 inputs the tomographic image 15 to the SS model 60 as the input image. Then, an output image 65 and the presence probability 66 are output from the SS model 60. In addition, the first derivation unit 43 generates positional information 67 from the output image 65. The first derivation unit 43 outputs the presence probability 66 and the positional information 67 to the second derivation unit 44 or the like as indirect finding information 51.

The output image 65 is an image in which the above seven classes are labeled for each pixel of the tomographic image 15. The entire pancreas 16 is labeled in any tomographic image 15, but a portion illustrating the indirect finding may not be labeled in a case in which it is not depicted in the original tomographic image 15.

The presence probability 66 is the presence probability of each of the above-described six types of indirect findings. The positional information 67 is information that represents a position of each of the above-described six types of indirect findings. More specifically, the positional information 67 is information in which position coordinates of the pixels labeled in the output image 65 are registered for each indirect finding. The presence probability 66 is an example of a "presence probability of the indirect finding" according to the technology of the present disclosure. The positional information 67 is an example of "positional information of the indirect finding" according to the technology of the present disclosure.

Figure 6:
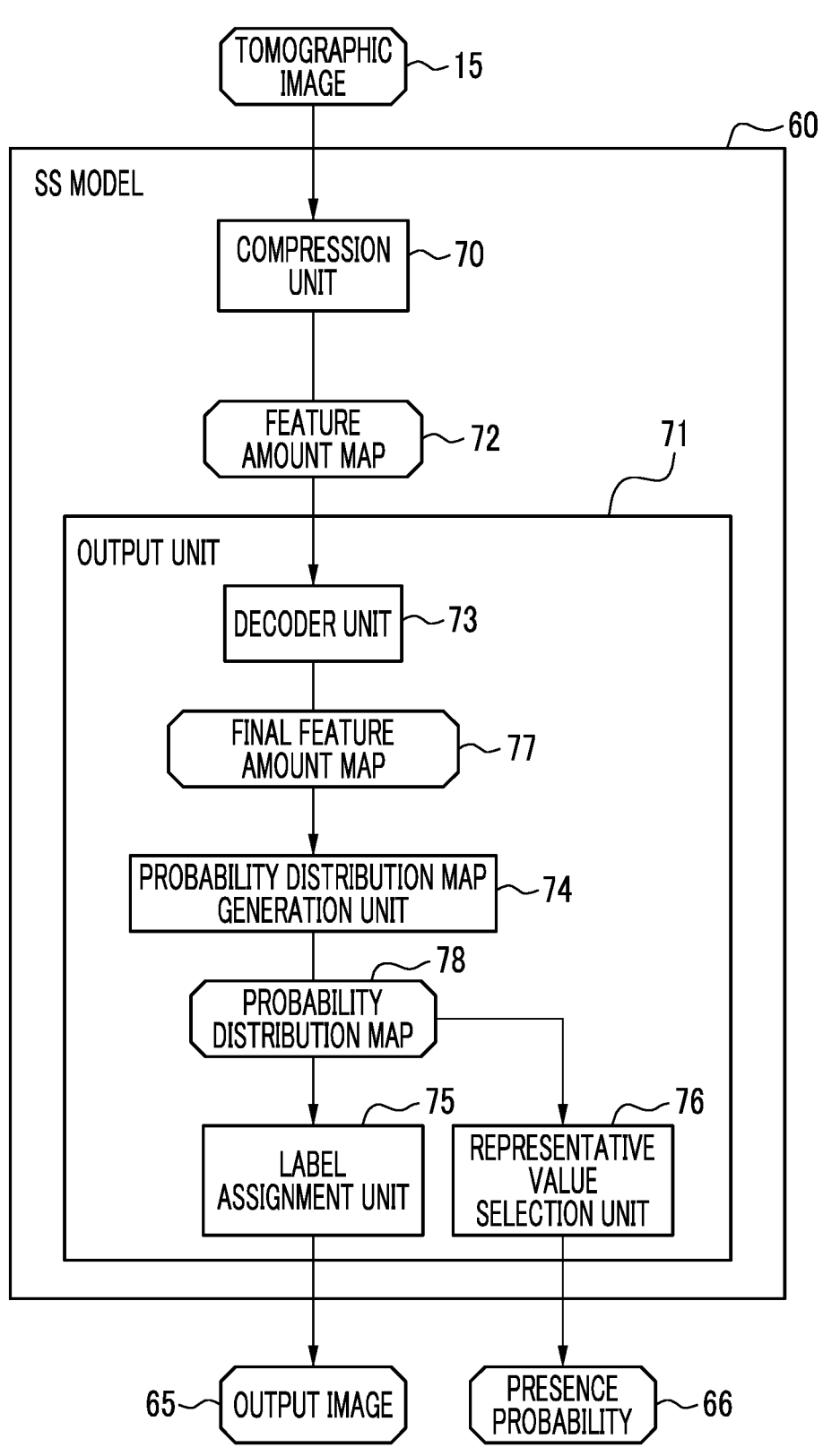
FIG. 6 is a diagram illustrating a detailed configuration of the SS model.

As an example, as illustrated in FIG. 6, the SS model 60 is composed of a compression unit 70 and an output unit 71. The compression unit 70 includes a plurality of convolution layers for the convolution processing using a filter, and a plurality of pooling layers for the pooling processing of reducing the data after the convolution processing by obtaining local statistics of the data after the convolution processing. The compression unit 70 converts the tomographic image 15 into a feature amount map 72. The compression unit 70 outputs the feature amount map 72 to the output unit

71. Although not illustrated, the compression unit 70 also performs skip layer processing or the like of delivering the data after the convolution processing to the output unit 71.

The output unit 71 includes a decoder unit 73, a probability distribution map generation unit 74, a label assignment unit 75, and a representative value selection unit 76. The decoder unit 73 performs upsampling processing of enlarging the feature amount map 72 to obtain an enlarged feature amount map. The decoder unit 73 also performs convolution processing simultaneously with the upsampling processing. In addition, the decoder unit 73 performs merge processing of combining the enlarged feature amount map with the data after the convolution processing which is delivered from the compression unit 70 in the skip layer processing. The decoder unit 73 further performs the convolution processing after the merge processing. Through such various pieces of processing, the decoder unit 73 uses the feature amount map 72 as a final feature amount map 77.

The final feature amount map 77 is also referred to as logits, and has elements corresponding to the pixels of the tomographic image 15 on a one-to-one basis. Each element of the final feature amount map 77 has an element value related to each class. The decoder unit 73 outputs the final feature amount map 77 to the probability distribution map generation unit 74.

The probability distribution map generation unit 74 generates the probability distribution map 78 from the final feature amount map 77 using a known activation function such as a softmax function. The probability distribution map generation unit 74 outputs the probability distribution map 78 to the label assignment unit 75 and the representative value selection unit 76.

Figure 7:
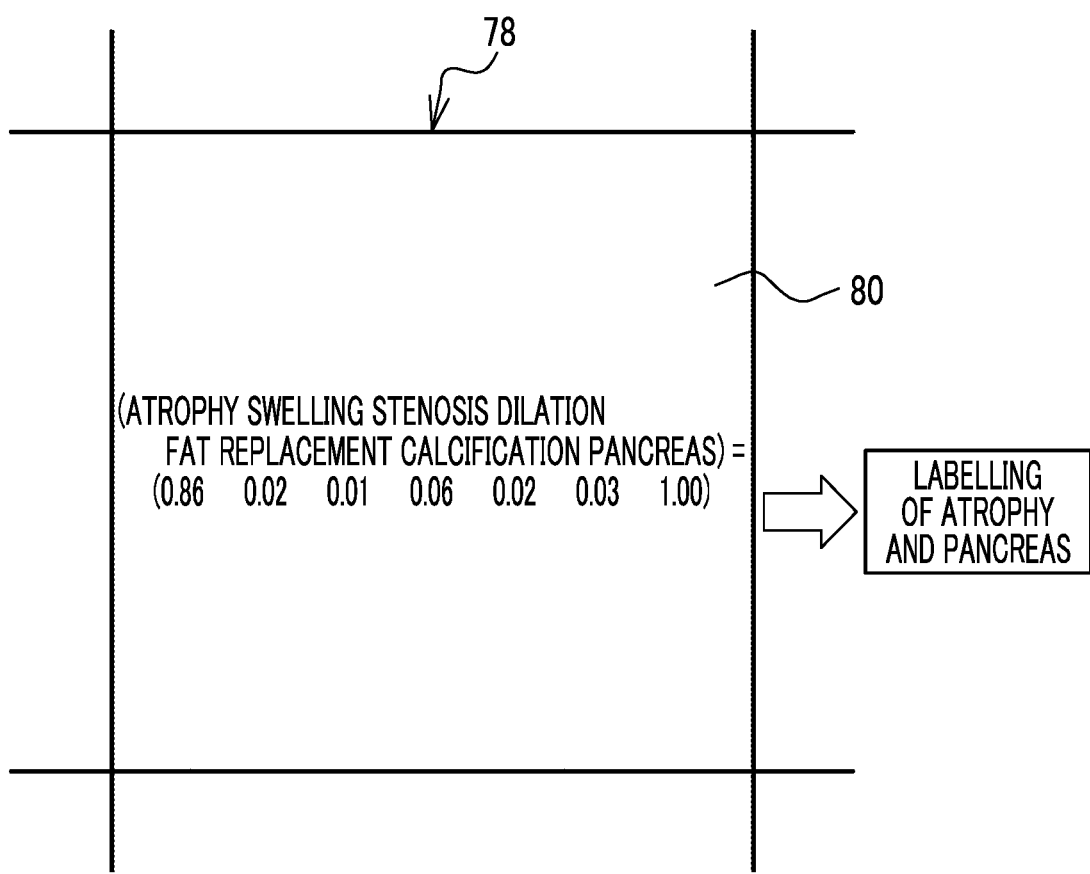
FIG. 7 is a diagram illustrating elements of a probability distribution map.

As an example, as illustrated in FIG. 7, the probability distribution map 78, similar to the final feature amount map 77, has elements 80 corresponding to the pixels of the tomographic image 15 on a one-to-one basis, and is data in which the presence probability of each class is registered as the element value of each element 80. FIG. 7 illustrates a case in which the probability that the element 80 is the part indicating atrophy, that is, the presence probability of atrophy is 86% (0.86), and the presence probabilities of swelling, stenosis, dilation, fat replacement, and calcification are 2%, 1%, 6%, 2%, and 3%, respectively. In addition, FIG. 7 illustrates a case in which the presence probability of the pancreas 16 is 100%. The presence probability of the indirect findings is 100% when all are added.

The label assignment unit 75 labels each element 80 of the probability distribution map 78 with a class in which the presence probability is equal to or higher than a preset threshold value. The label assignment unit 75 does not label the element 80 for which the presence probability of each class is less than the threshold value with a class. The threshold value is, for example, 80%. Therefore, in the example illustrated in FIG. 7, the label assignment unit 75 labels the atrophy with a presence probability of 86% and the pancreas 16 with a presence probability of 100%.

The representative value selection unit 76 selects a representative value of the presence probability for each class of indirect findings. The representative value is, for example, a maximum value or a mode value. The representative value selection unit 76 outputs the selected representative value as the presence probability 66.

Figure 8:
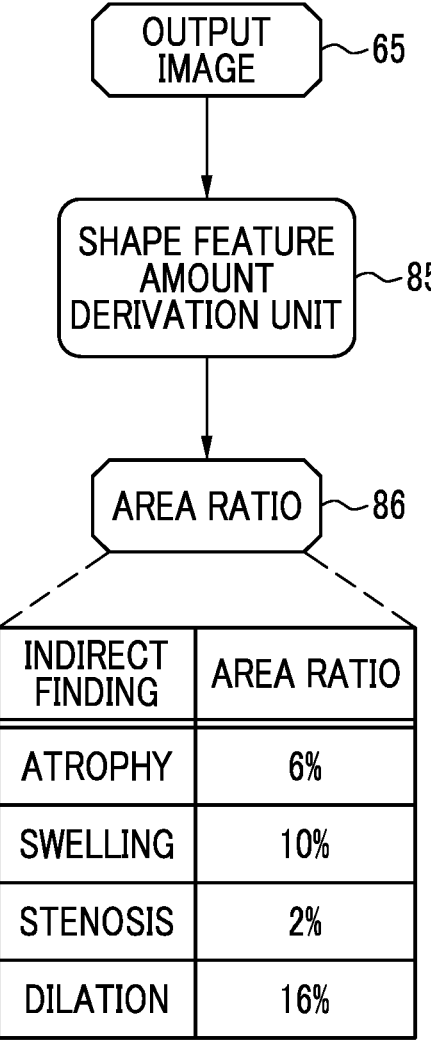
FIG. 8 is a diagram illustrating processing by a shape feature amount derivation unit.

As an example, as illustrated in FIG. 8, the first derivation unit 43 includes a shape feature amount derivation unit 85. The output image 65 is input to the shape feature amount derivation unit 85. The shape feature amount derivation unit 85 calculates an area ratio 86 of a portion indicating shape indirect findings (atrophy, swelling, stenosis, and dilation) to the entire pancreas 16 based on the output image 65. More specifically, the shape feature amount derivation unit 85 divides the number of pixels labeled in the portion indicating each shape indirect finding in the output image 65 by the number of pixels labeled in the pancreas 16 to calculate the area ratio 86. The shape feature amount derivation unit 85 outputs the area ratio 86 as the indirect finding information 51 to the second derivation unit 44 and the like. The area ratio 86 is an example of a "shape feature amount of the indirect finding" according to the technology of the present disclosure. The area ratio 86 of the portion indicating a property indirect finding may be calculated.

Figure 9:
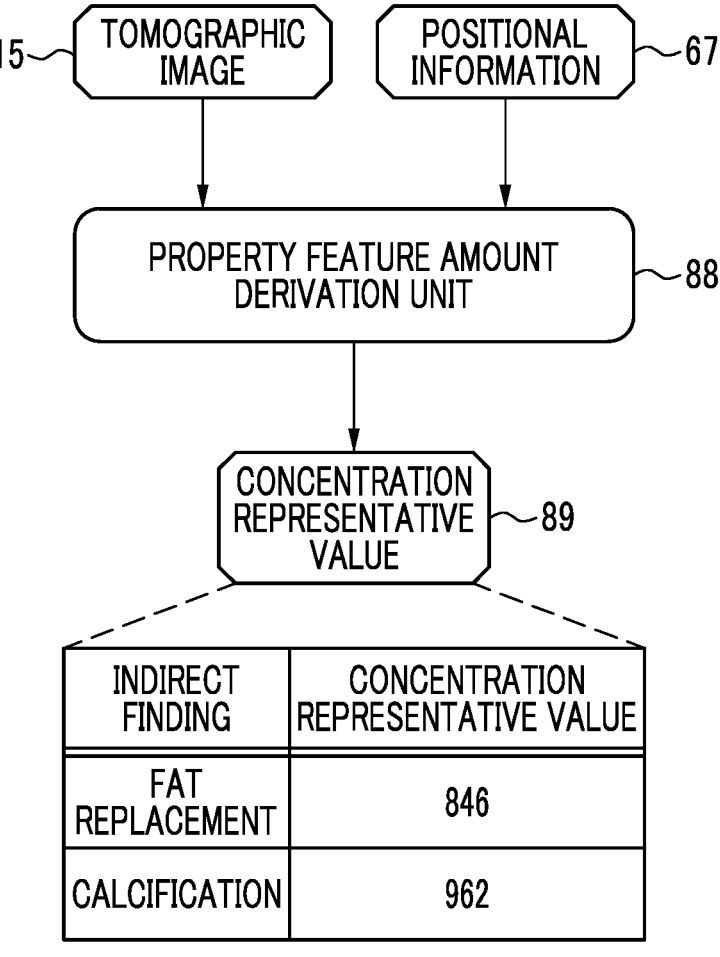
FIG. 9 is a diagram illustrating processing by a property feature amount derivation unit.

As an example, as illustrated in FIG. 9, the first derivation unit 43 includes a property feature amount derivation unit 88. The tomographic image 15 and the positional information 67 are input to the property feature amount derivation unit 88. The property feature amount derivation unit 88 derives a concentration representative value 89, which is a representative value of a pixel value of a portion indicating property indirect findings (fat replacement and calcification), based on the tomographic image 15 and the positional information 67. More specifically, the property feature amount derivation unit 88 specifies the pixel of the portion indicating the property indirect finding in the tomographic image 15, from the positional information 67. Then, for example, the maximum value, the minimum value, the mode value, or the average value of the pixel values of the specified pixels is derived as the concentration representative value 89. The property feature amount derivation unit 88 outputs the concentration representative value 89 as the indirect finding information 51 to the second derivation unit 44 or the like. The concentration representative value 89 is an example of the "property feature amount of the indirect finding" according to the technology of the present disclosure. The concentration representative value 89 of the portion indicating the shape indirect finding may be derived.

Figure 10:
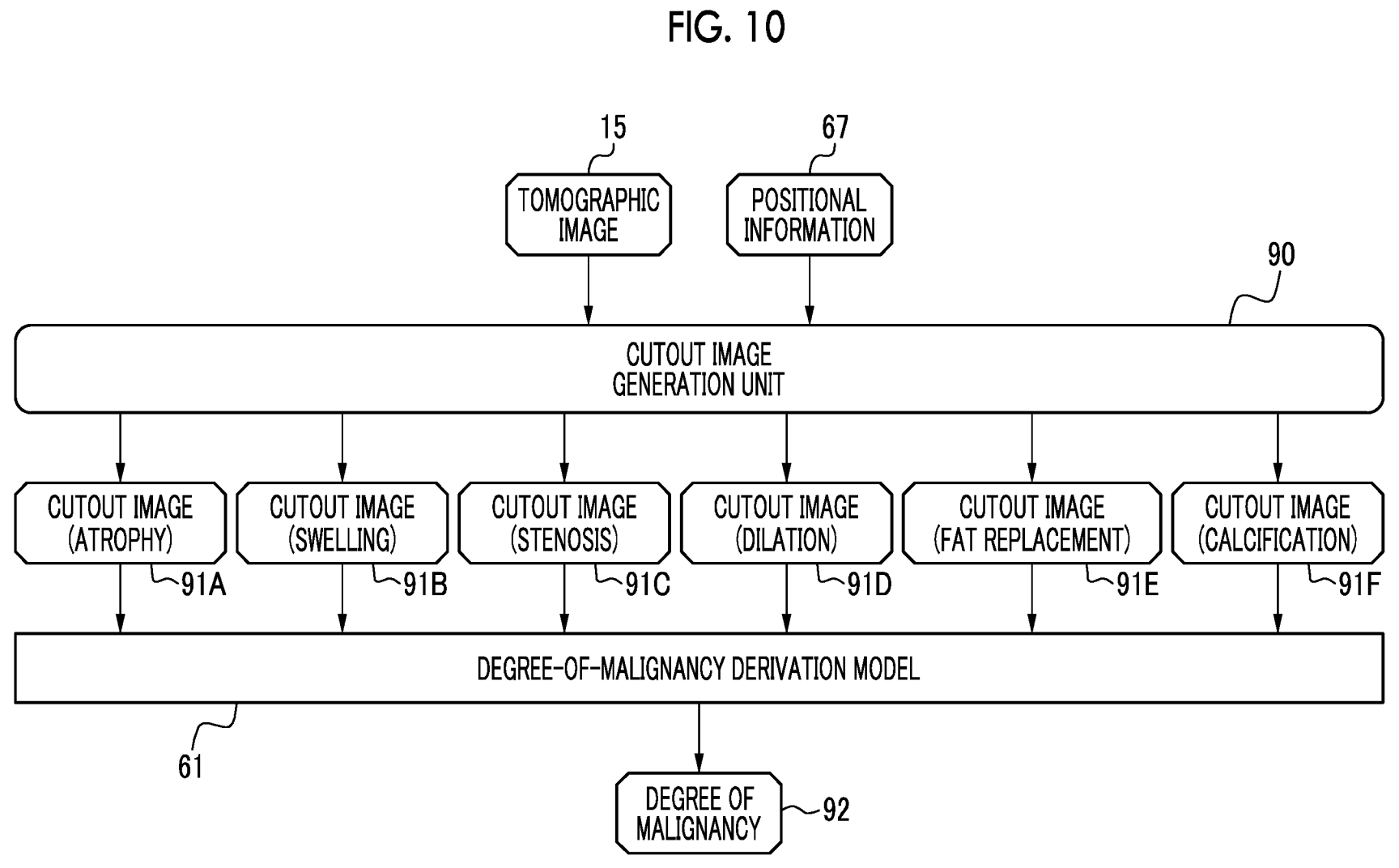

As an example, as illustrated in FIG. 10, the first derivation unit 43 includes a cutout image generation unit 90. The tomographic image 15 and the positional information 67 are input to the cutout image generation unit 90. The cutout image generation unit 90 generates cutout images 91A, 91B, 91C, 91D, 91E, and 91F in which a portion indicating each indirect finding is cut out in a box shape from the tomographic image 15 based on the positional information 67. The cutout image 91A is a cutout image of a part indicating atrophy, the cutout image 91B is a cutout image of a part indicating swelling, the cutout image 91C is a cutout image of a part indicating stenosis, and the cutout image 91D is a cutout image of a part indicating dilation. In addition, the cutout image 91E is a cutout image of a portion indicating fat replacement, and the cutout image 91F is a cutout image of a portion indicating calcification.

The first derivation unit 43 inputs the cutout images 91A to 91F to the degree-of-malignancy derivation model 61. Similar to the SS model 60, the degree-of-malignancy derivation model 61 is configured by a convolutional neural network. The degree-of-malignancy derivation model 61 derives a degree of malignancy 92 of the tumor based on the indirect finding based on the cutout images 91A to 91F. The degree of malignancy 92 is, for example, 10 grades of 1 to 10, and the larger the value, the higher the probability that the tumor is malignant. The first derivation unit 43 outputs the degree of malignancy 92 as the indirect finding information 51 to the second derivation unit 44 or the like. The degree of malignancy 92 is an example of "degree of malignancy of the lesion based on the indirect finding" according to the technology of the present disclosure.

Figure 11:
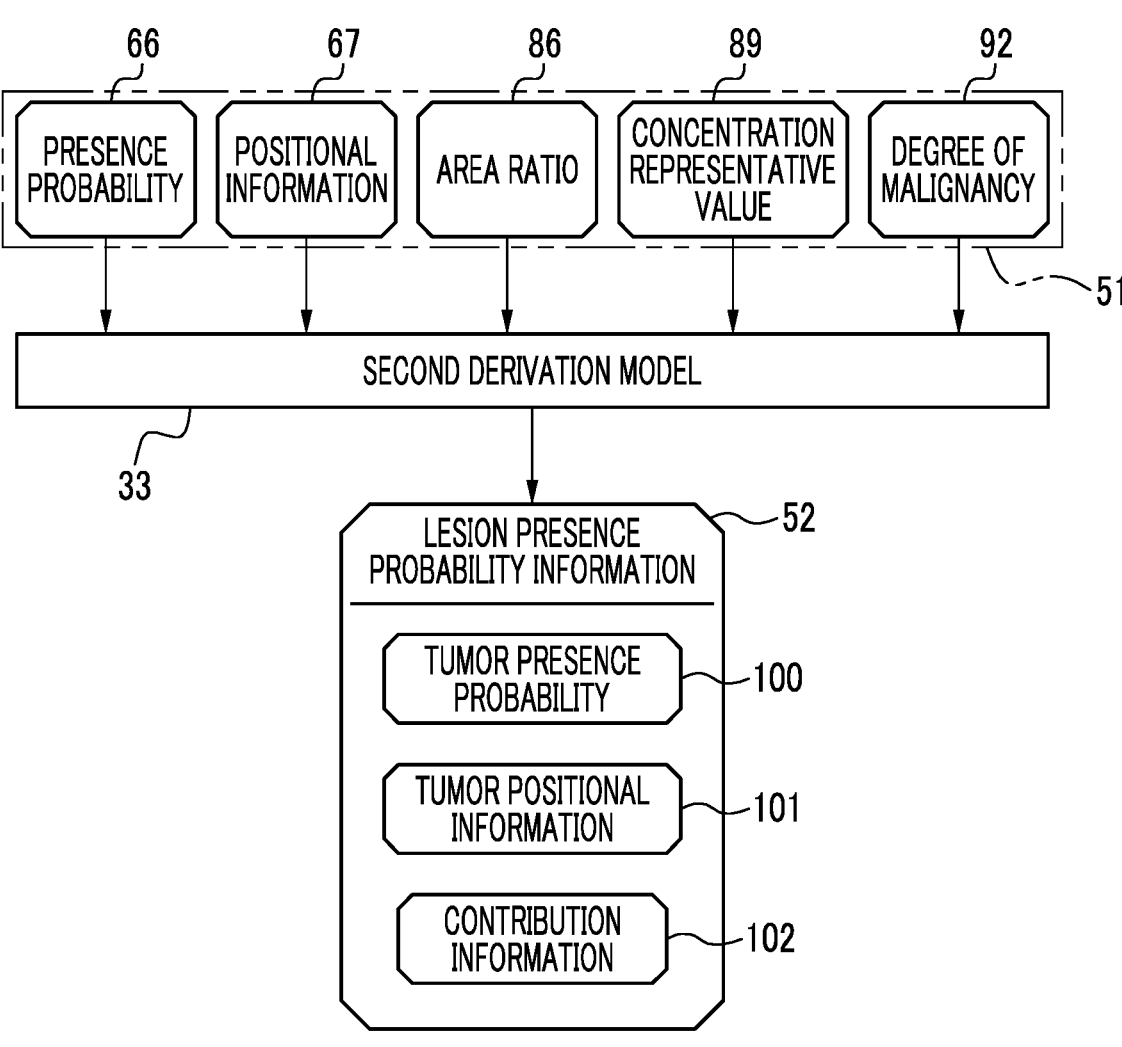
FIG. 11 is a diagram illustrating processing by a second derivation model.

As an example, as illustrated in FIG. 11, the second derivation unit 44 inputs the indirect finding information 51 that is composed of the presence probability 66, the positional information 67, the area ratio 86, the concentration representative value 89, and the degree of malignancy 92 to the second derivation model 33. The second derivation model 33 is constructed by, for example, a linear discriminant analysis method or a boosting method such as the extreme gradient boosting (XGBoost). The second derivation model 33 outputs the lesion presence probability information 52 based on the indirect finding information 51.

The lesion presence probability information 52 includes a tumor presence probability 100, a tumor positional information 101, and a contribution information 102. The tumor presence probability 100 represents a presence probability of the tumor in the pancreas 16. The tumor positional information 101 is information in which the position coordinates of pixels of a portion that seems to be a tumor are registered. The tumor presence probability 100 is an example of the "lesion presence probability" according to the technology of the present disclosure. The tumor positional information 101 is an example of "positional information of the lesion" according to the technology of the present disclosure.

Since the second derivation model 33 is constructed by the linear discriminant analysis method or the boosting method, it is possible to derive the contribution information 102. As an example, as illustrated in FIG. 12, the contribution information 102 is information in which the contribution to the derivation of the tumor presence probability 100 and the tumor positional information 101 is registered for each indirect finding information 51 (the presence probability 66, the positional information 67, the area ratio 86, the concentration representative value 89, and the degree of malignancy 92). The indirect finding information 51 that contributes deeply to the derivation of the tumor presence probability 100 and the tumor positional information 101 has a larger contribution.

Figure 13:
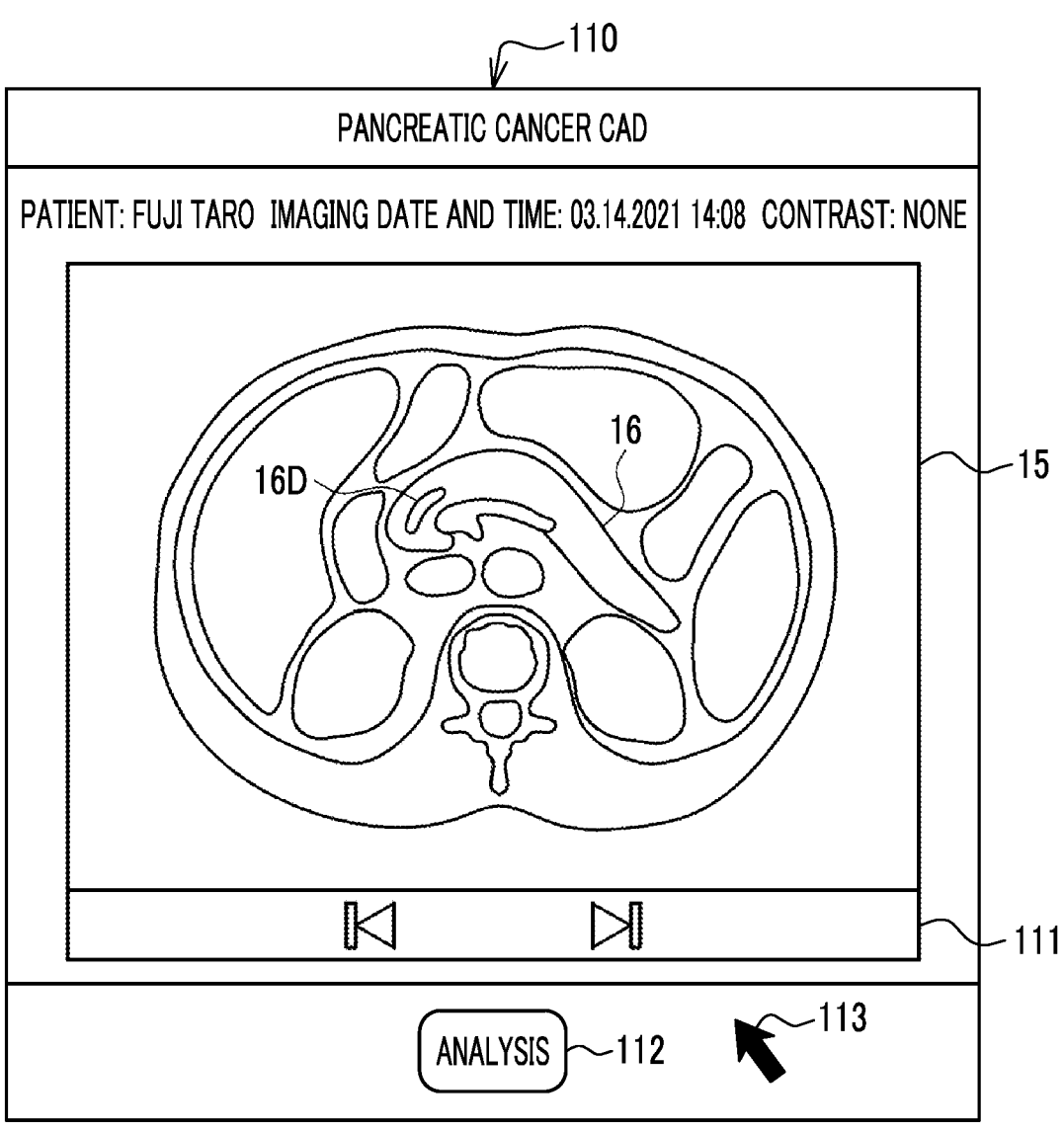
FIG. 13 is a diagram illustrating a first screen.

In a case in which the tomographic image 15 in response to the image distribution request 50 is transmitted from the PACS server 11, the first screen 110 illustrated in FIG. 13 is displayed on the display 17 as an example under the control of the display control unit 45. On the first screen 110, a patient name, an imaging date and time, the presence or absence of contrast, and the tomographic image 15 are displayed. An operation button group 111 for sending back the displayed tomogram of the tomographic image 15 is disposed at the lower part of the tomographic image 15. In addition, an analysis button 112 is disposed at the lower part of the first screen 110.

In a case in which the doctor desires to check whether or not there is a tumor that is not depicted in the pancreas 16 shown in the tomographic image 15, the doctor moves a cursor 113 to the analysis button 112 and selects it. In a case in which the analysis button 112 is selected, an analysis instruction for the tomographic image 15 is input to the instruction receiving unit 40. Accordingly, the first derivation unit 43 and the second derivation unit 44 are operated, the indirect finding information 51 is derived by the first derivation unit 43, and the lesion presence probability information 52 is derived by the second derivation unit 44.

Figure 14:
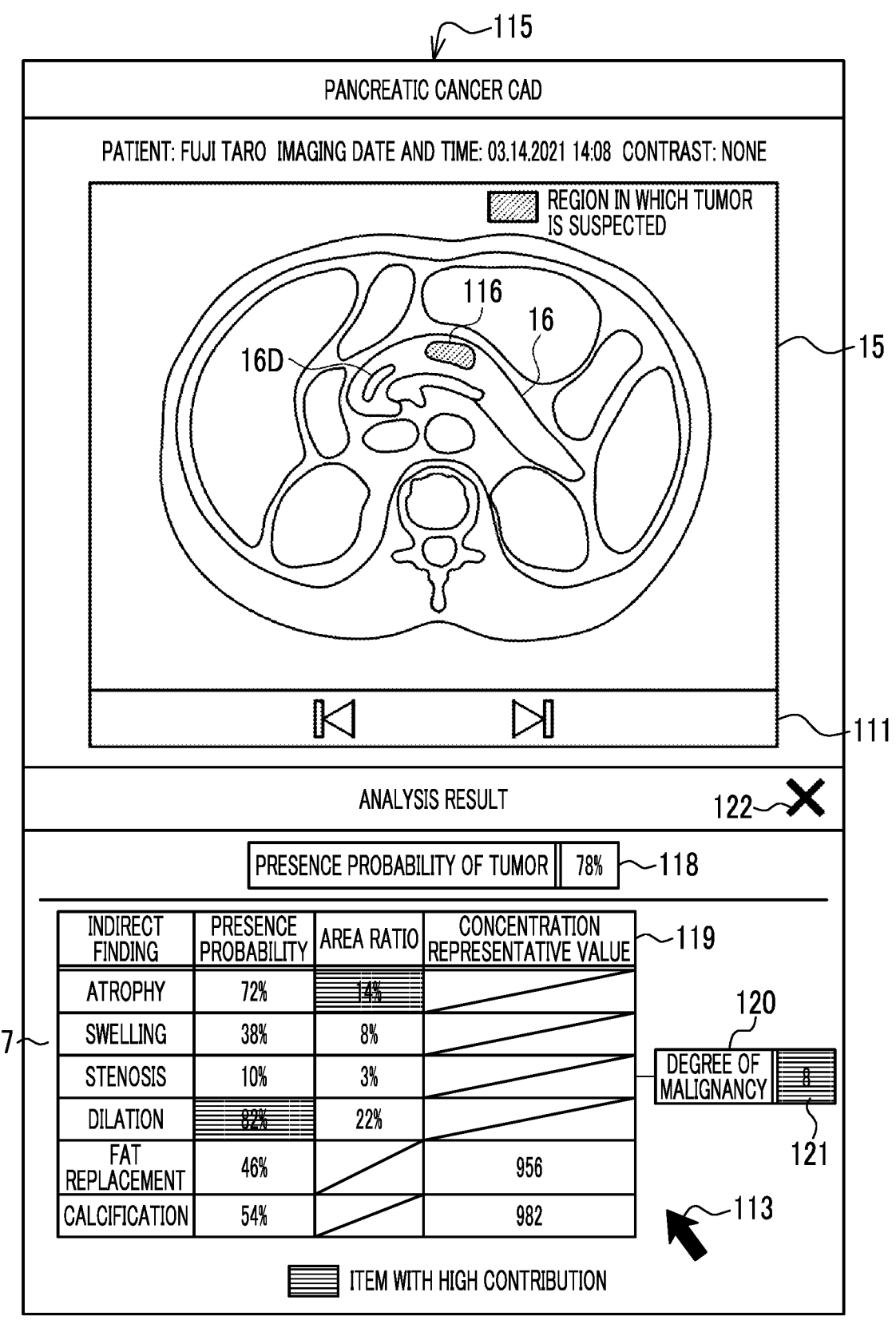
FIG. 14 is a diagram illustrating a second screen.

After the analysis button 112 is selected, the first screen 110 transitions to the second screen 115 illustrated in FIG. 14 as an example. On the tomographic image 15 of the second screen 115, a marker 116 indicating a region in which the tumor is suspected in the pancreas 16 is displayed based on the tumor positional information 101 of the lesion presence probability information 52. The marker 116 fills, for example, the pixel of the portion that seems to be a tumor registered in the tumor positional information 101 with red.

The second screen 115 has an analysis result display region 117 based on the indirect finding information 51 and the lesion presence probability information 52 at the lower part of the second screen 115. In the analysis result display region 117, a display frame 118 of the tumor presence probability 100, a display frame 119 of the presence probability 66 of each indirect finding, the area ratio 86 of the shape indirect finding, and the concentration representative value 89 of the property indirect finding, and a display frame 120 of the degree of malignancy 92 are provided. By displaying the second screen 115 on the display 17, the display control unit 45 presents the indirect finding information 51 and the lesion presence probability information 52 to the doctor.

In the display frames 119 and 120, the display control unit 45 performs, for example, red hatching 121 on the indirect finding information 51 having the top three contributions registered in the contribution information 102. The display control unit 45 distinguishes the indirect finding information 51 having the top three contributions to the derivation of the lesion presence probability information 52 from the indirect finding information 51 having a contribution lower than the third by the hatching 121. The indirect finding information 51 having the top three contributions is an example of "indirect finding information having a relatively high contribution" according to the technology of the present disclosure. In addition, the indirect finding information 51 having a contribution lower than the third is an example of "indirect finding information having a relatively low contribution" according to the technology of the present disclosure.

FIG. 14 illustrates a case in which the contributions of the presence probability 66 of the dilation, the area ratio 86 of the atrophy, and the degree of malignancy 92 are the top three. The display of the analysis result display region 117 disappears by selecting the close button 122. Accordingly, the second screen 115 returns to the first screen 110.

Next, an action of the above-described configuration will be described with reference to the flowcharts illustrated in FIG. 15 and FIG. 16 as an example. First, in a case in which the operation program 30 is started in the doctor terminal 12, as illustrated in FIG. 3, the CPU 22 of the doctor terminal 12 functions as the instruction receiving unit 40, the image acquisition unit 41, the RW control unit 42, the first derivation unit 43, the second derivation unit 44, and the display control unit 45.

In FIG. 15, in a case in which a search keyword is input by a doctor via the input device 18 and an image distribution instruction is received in the instruction receiving unit 40 (YES in Step ST100), the search keyword is output from the instruction receiving unit 40 to the image acquisition unit 41. Then, the image distribution request 50 including the search keyword is transmitted to the PACS server 11 from the image acquisition unit 41 (Step ST110). In the PACS server 11, the tomographic image 15 in response to the image distribution request 50 is searched, and the searched tomographic image 15 is distributed to the image acquisition unit 41. The tomographic image 15 distributed from the PACS server 11 is acquired by the image acquisition unit 41 (Step ST120). The tomographic image 15 is output from the image acquisition unit 41 to the RW control unit 42, and is stored in the storage 20 by the RW control unit 42. In addition, as illustrated in FIG. 13, the first screen 110 including the tomographic image 15 is displayed on the display 17 under the control of the display control unit 45 (Step ST130).

In FIG. 16, in a case in which the analysis button 112 of the first screen 110 is selected by the doctor and the analysis instruction of the tomographic image 15 is received by the instruction receiving unit 40 (YES in Step ST200), the fact is output to the first derivation unit 43 and the second derivation unit 44. Then, as illustrated in FIGS. 5 to 10, indirect finding information 51 is derived from the tomographic image 15 using the first derivation model 32 in the first derivation unit 43 (Step ST210). The indirect finding information 51 is output from the first derivation unit 43 to the second derivation unit 44 and the display control unit 45.

Next, as illustrated in FIG. 11, in the second derivation unit 44, the lesion presence probability information 52 is derived from the indirect finding information 51 using the second derivation model 33 (Step ST220). The lesion presence probability information 52 is output from the second derivation unit 44 to the display control unit 45.

As illustrated in FIG. 14, the second screen 115 including the analysis result display region 117 based on the indirect finding information 51 and the lesion presence probability information 52 is displayed on the display 17 under the control of the display control unit 45 (Step ST230).

As described above, the CPU 22 of the doctor terminal 12 comprises the image acquisition unit 41, the first derivation unit 43, and the second derivation unit 44. The image acquisition unit 41 acquires the tomographic image 15 distributed from the PACS server 11 in response to the image distribution request 50. The first derivation unit 43 analyzes the tomographic image 15 to derive the indirect finding information 51 related to the indirect finding that represents features of the shape and the property of the peripheral tissue of the tumor associated with the occurrence of the tumor. The second derivation unit 44 derives the lesion presence probability information 52 indicating the presence probability of the tumor based on the indirect finding information 51. For this reason, it is possible to contribute to the detection of a tumor that is hardly depicted by using a method based on the thought of the doctor of using the indirect finding to detect the tumor that is hardly depicted as a clue.

As illustrated in FIG. 11, the indirect finding information 51 includes the presence probability 66, the positional information 67, the area ratio 86 of the shape indirect finding, the concentration representative value 89 of the property indirect finding, and the degree of malignancy 92 of the tumor based on the indirect finding. Therefore, the features of the indirect findings can be expressed more succinctly.

In addition, as illustrated in FIG. 11, the lesion presence probability information 52 includes the tumor presence probability 100 and the tumor positional information 101. Therefore, the presence probability of the tumor can be accurately represented.

As illustrated in FIG. 14, the display control unit 45 presents the indirect finding information 51 and the lesion presence probability information 52 to the doctor. Therefore, the doctor can make a diagnosis of the pancreatic cancer while referring not only to the tomographic image 15 but also to the indirect finding information 51 and the lesion presence probability information 52. It is possible to reduce the burden on the doctor for diagnosis.

In addition, as illustrated in FIG. 14, the display control unit 45 presents, by the hatching 121, the indirect finding information 51 having a relatively high contribution to the derivation of the lesion presence probability information 52 as distinguished from the indirect finding information 51 having a relatively low contribution to the doctor. Therefore, the doctor can see at a glance the indirect finding information 51 having a relatively high contribution. The doctor can verify the validity of the lesion presence probability information 52.

The lesion is a tumor. Therefore, it is possible to derive the lesion presence probability information 52 of the tumor directly related to pancreatic cancer.

The shape indirect finding includes atrophy, swelling, stenosis, and dilation, and the property indirect finding includes fat replacement and calcification. These indirect findings frequently occur in the peripheral tissue of the tumor as the tumor develops. Therefore, by deriving the lesion presence probability information 52 based on the indirect finding information 51 of these indirect findings, the reliability of the lesion presence probability information 52 can be improved.

The medical image is a non-contrast tomographic image 15 of the abdomen on which the pancreas 16 is shown and is used for diagnosing the pancreatic cancer. Since the tumor related to the pancreatic cancer is hardly depicted in the non-contrast tomographic image 15, it is possible to fully exert the effect of the technology of the present disclosure that it is possible to contribute to the detection of the tumor that is hardly depicted. In addition, the non-contrast tomographic image 15 has less burden on the patient P at the time of imaging than the contrast tomographic image. Therefore, if the non-contrast tomographic image 15 opens a way for detecting a tumor with a high probability, it is possible to diagnose pancreatic cancer without capturing a contrast tomographic image that places a relatively large burden on the patient P.

Although the tumor related to the pancreatic cancer is exemplified as the lesion, but the present disclosure is not limited thereto. As an example, as illustrated in FIG. 17, the lesion may be a cyst (neoplastic pancreatic cyst) related to the pancreatic cancer.

Figure 17:
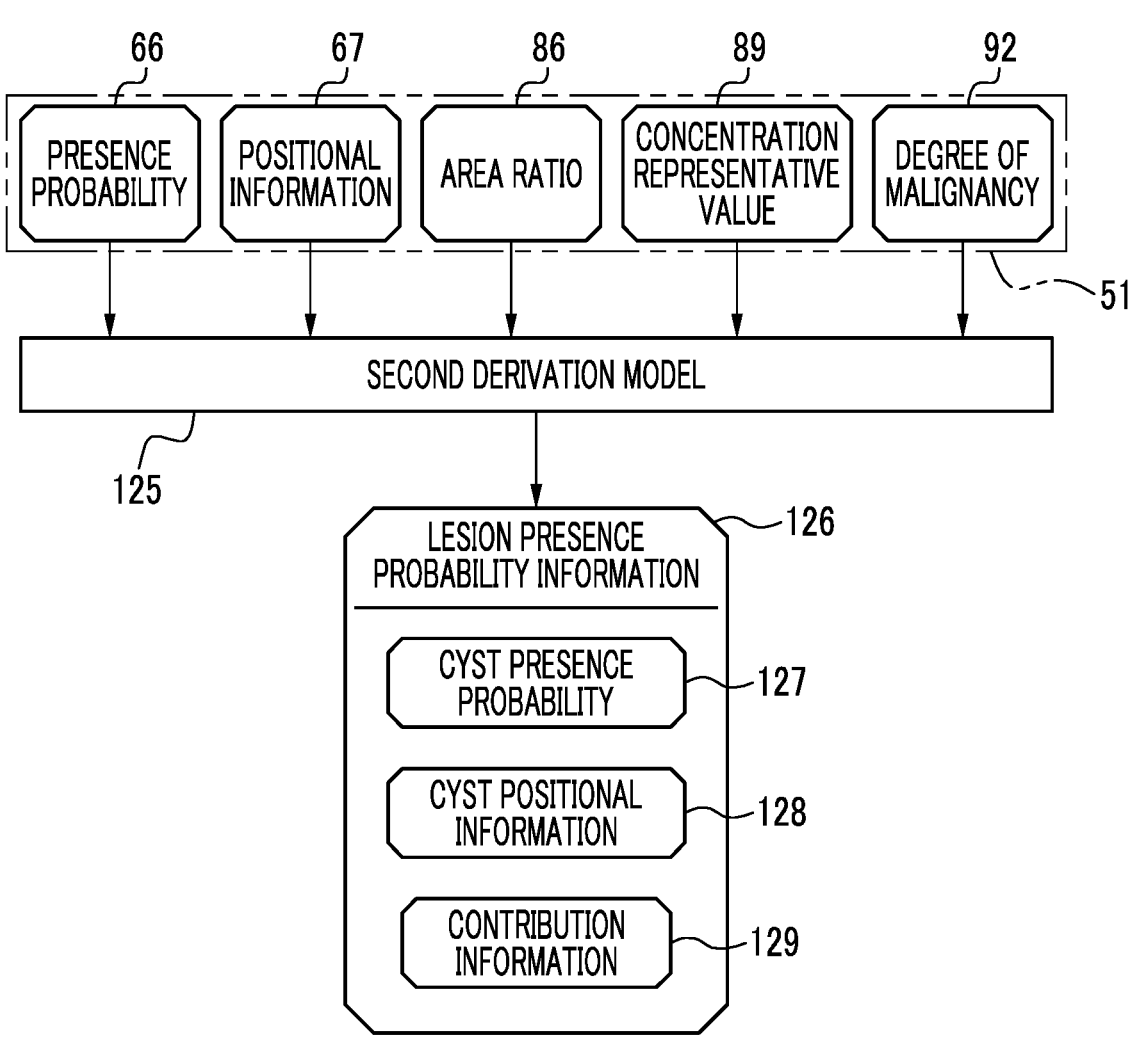
FIG. 17 is a diagram illustrating another example of processing by the second derivation model.

In FIG. 17, the second derivation model 125 outputs the lesion presence probability information 126 based on the indirect finding information 51. The lesion presence probability information 126 includes a cyst presence probability 127, a cyst positional information 128, and a contribution information 129. The cyst presence probability 127 represents the presence probability of a cyst in the pancreas 16. The cyst positional information 128 is information in which the position coordinates of pixels of a portion that seems to be a cyst are registered. The contribution information 129 is information in which the contribution to the derivation of the cyst presence probability 127 and the cyst positional information 128 are registered for each indirect finding information 51. The cyst presence probability 127 is an example of the "lesion presence probability" according to the technology of the present disclosure. The cyst positional information 128 is an example of "positional information of the lesion" according to the technology of the present disclosure. It is possible to derive the lesion presence probability information 126 of the cyst directly related to pancreatic cancer. Both the lesion presence probability information 52 of the tumor and the lesion presence probability information 126 of the cyst may be derived.

Second Embodiment

In the second embodiment illustrated in FIGS. 18 to 27, the tomographic image 15 in which the tumor is visibly depicted is also the analysis target.

Figure 18:
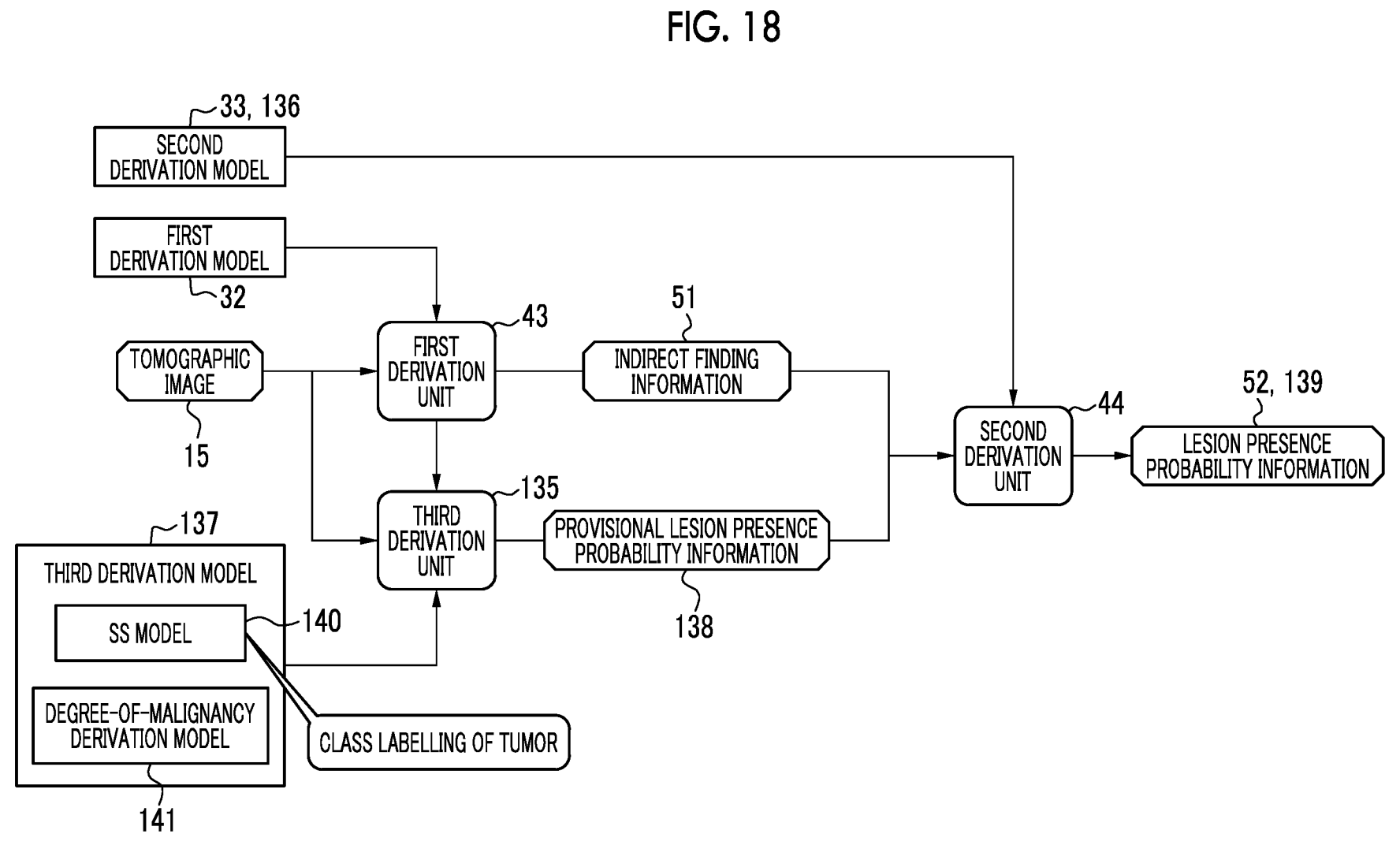

As an example, as illustrated in FIG. 18, a CPU of a doctor terminal of the second embodiment functions as a third derivation unit 135, in addition to the processing units 40 to 45 (the units other than the first derivation unit 43 and the second derivation unit 44 are not illustrated in FIG. 18) of the above-described first embodiment. In addition, in the storage of the doctor terminal 12 of the second embodiment, a second derivation model 136 and a third derivation model 137 are stored in addition to the tomographic image 15, the first derivation model 32, and the second derivation model 33.

The tomographic image 15 and the first derivation model 32 are read from the storage by the RW control unit 42 and output from the RW control unit 42 to the first derivation unit 43, as in the first embodiment. The second derivation models 33 and 136 are read from the storage by the RW control unit 42 and output from the RW control unit 42 to the second derivation unit 44. In addition, the tomographic image 15 and the third derivation model 137 are read from the storage by the RW control unit 42 and output from the RW control unit 42 to the third derivation unit 135.

The first derivation unit 43 derives the indirect finding information 51 from the tomographic image 15 using the first derivation model 32 as in the first embodiment. The first derivation unit 43 outputs the indirect finding information 51 to the second derivation unit 44. The third derivation unit 135 derives provisional lesion presence probability information 138 from the tomographic image 15 using the third derivation model 137. The provisional lesion presence probability information 138 is information indicating the provisional presence probability of the tumor, which represents at least one feature of the shape or the property of the tumor that is visibly depicted. The third derivation unit 135 outputs the provisional lesion presence probability information 138 to the second derivation unit 44 and the display control unit 45. The second derivation unit 44 derives the lesion presence probability information 52 from the indirect finding information 51 using the second derivation model 33 as in the first embodiment. In addition, the second derivation unit 44 derives the lesion presence probability information 139 based on the indirect finding information 51 and the provisional lesion presence probability information 138 using the second derivation model 136. The second derivation unit 44 outputs the lesion presence probability information 139 to the display control unit 45. In addition, "provisional" means that the lesion presence probability information 139 to be finally derived is provisional.

The third derivation model 137 includes an SS model 140 and a degree-of-malignancy derivation model 141. The SS model 140 is constructed by the convolutional neural network in the same manner as the SS model 60 of the first embodiment. The extraction object of the SS model 140 is a portion indicating a tumor.

Figure 19:
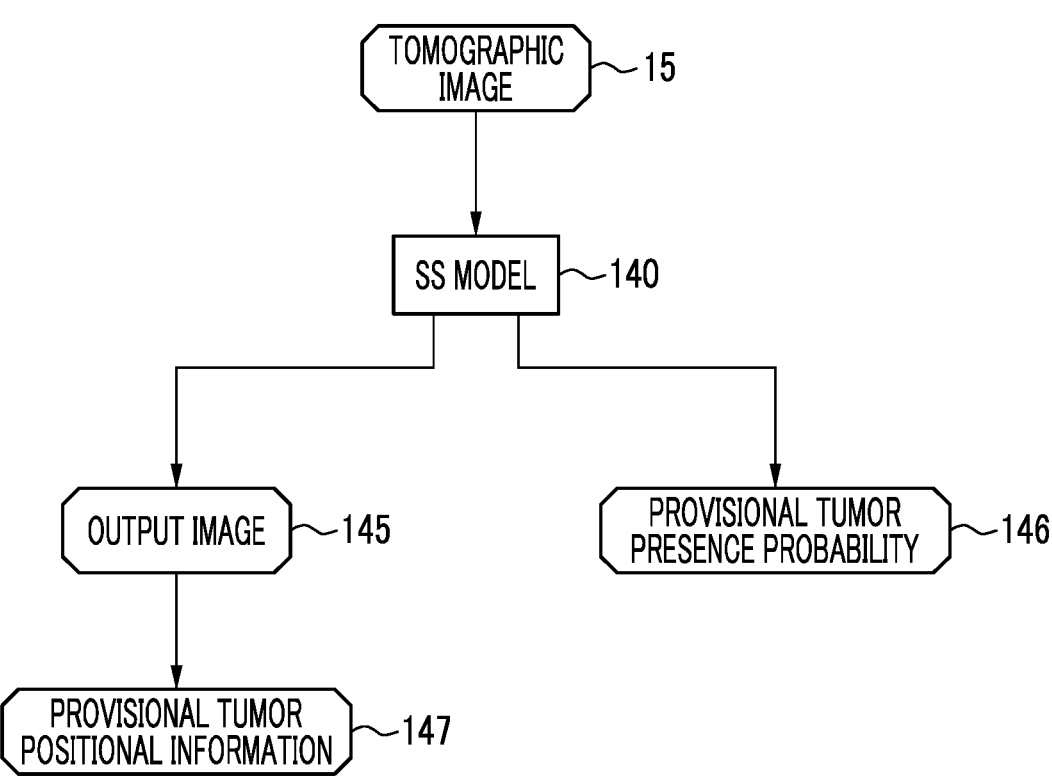
FIG. 19 is a diagram illustrating processing by an SS model of the second embodiment.

As an example, as illustrated in FIG. 19, the third derivation unit 135 inputs the tomographic image 15 to the SS model 140 as the input image. Then, an output image 145 and the provisional tumor presence probability 146 are output from the SS model 140. In addition, the third derivation unit 135 generates provisional tumor positional information 147 from the output image 145. The third derivation unit 135 outputs the provisional tumor presence probability 146 and the provisional tumor positional information 147 to the second derivation unit 44 or the like as the provisional lesion presence probability information 138. The provisional tumor presence probability 146 is an example of a "provisional presence probability of the lesion" according to the technology of the present disclosure. The provisional tumor positional information 147 is an example of "provisional positional information of the lesion" according to the technology of the present disclosure.

The output image 145 is an image in which a portion indicating a tumor is labeled as a class. The provisional tumor presence probability 146 is a provisional presence probability of the tumor. The provisional tumor positional information 147 is information that represents a provisional position of the tumor. More specifically, the provisional tumor positional information 147 is information in which the position coordinates of the pixels of the portion indicating the labeled tumor in the output image 145 are registered.

Similar to the SS model 60 of the first embodiment, the SS model 140 generates a probability distribution map indicating the presence probability of the tumor. Then, the SS model 140 outputs the provisional tumor presence probability 146 based on the probability distribution map.

Figure 20:
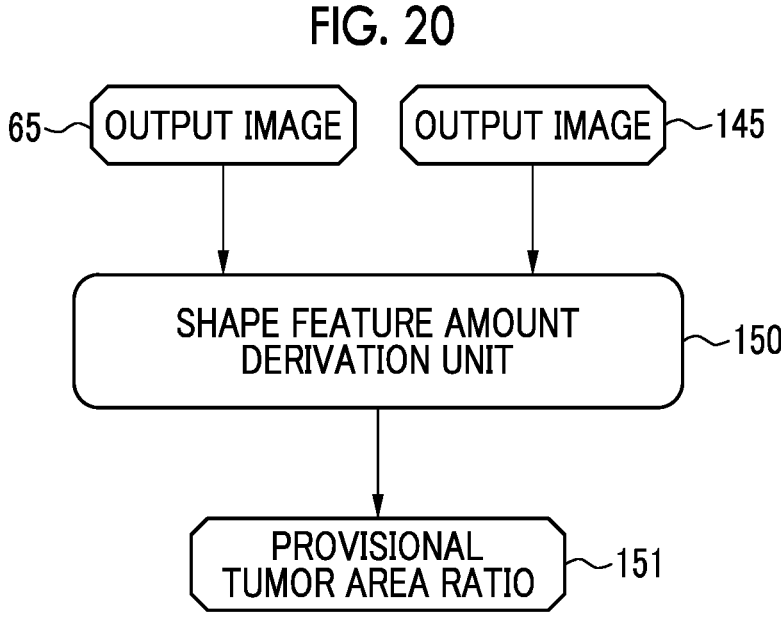
FIG. 20 is a diagram illustrating processing by a shape feature amount derivation unit of the second embodiment.

As an example, as illustrated in FIG. 20, the third derivation unit 135 includes a shape feature amount derivation unit 150. In the shape feature amount derivation unit 150, the output image 65 output by the SS model 60 and the output image 145 output by the SS model 140 are input. The shape feature amount derivation unit 150 calculates a provisional tumor area ratio 151, which is an area ratio of a portion indicating a tumor to the entire pancreas 16, based on the output images 65 and 145. More specifically, the shape feature amount derivation unit 150 divides the number of pixels labeled in the portion indicating the tumor of the output image 145 by the number of pixels labeled in the pancreas 16 of the output image 65 to calculate the provisional tumor area ratio 151. The shape feature amount derivation unit 150 outputs the provisional tumor area ratio 151 to the second derivation unit 44 or the like as the provisional lesion presence probability information 138. The provisional tumor area ratio 151 is an example of "provisional shape feature amount of the lesion" according to the technology of the present disclosure.

Figure 21:
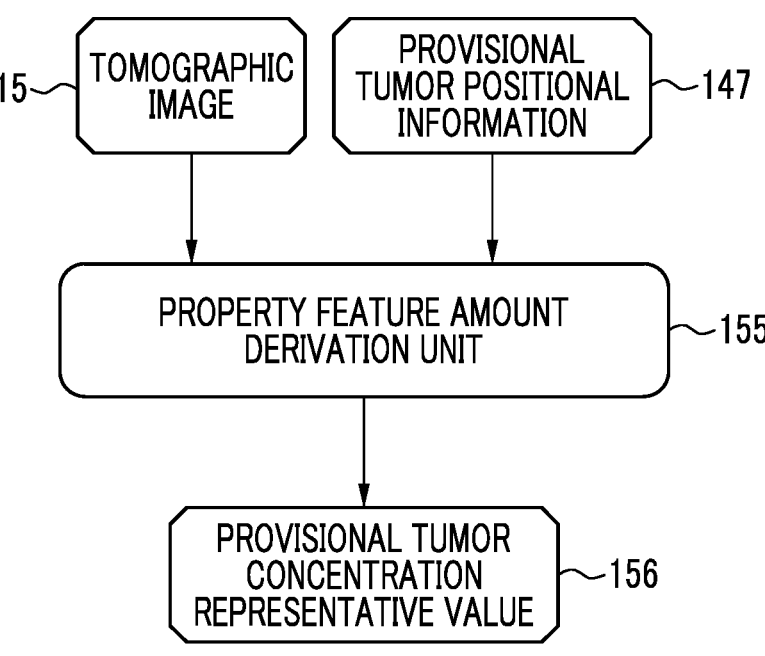
FIG. 21 is a diagram illustrating processing by a property feature amount derivation unit of the second embodiment.

As an example, as illustrated in FIG. 21, the third derivation unit 135 includes a property feature amount derivation unit 155. The tomographic image 15 and the provisional tumor positional information 147 are input to the property feature amount derivation unit 155. The property feature amount derivation unit 155 derives a provisional tumor concentration representative value 156, which is a representative value of a pixel value of a portion indicating the tumor, based on the tomographic image 15 and the provisional tumor positional information 147. More specifically, the property feature amount derivation unit 155 specifies the pixel of the portion indicating the tumor in the tomographic image 15 from the provisional tumor positional information 147. Then, for example, the maximum value, the minimum value, the mode value, or the average value of the pixel values of the specified pixels is derived as the provisional tumor concentration representative value 156. The property feature amount derivation unit 155 outputs the provisional tumor concentration representative value 156 to the second derivation unit 44 or the like as the provisional lesion presence probability information 138. The provisional tumor concentration representative value 156 is an example of a "provisional property feature amount of the lesion" according to the technology of the present disclosure.

Figure 22:
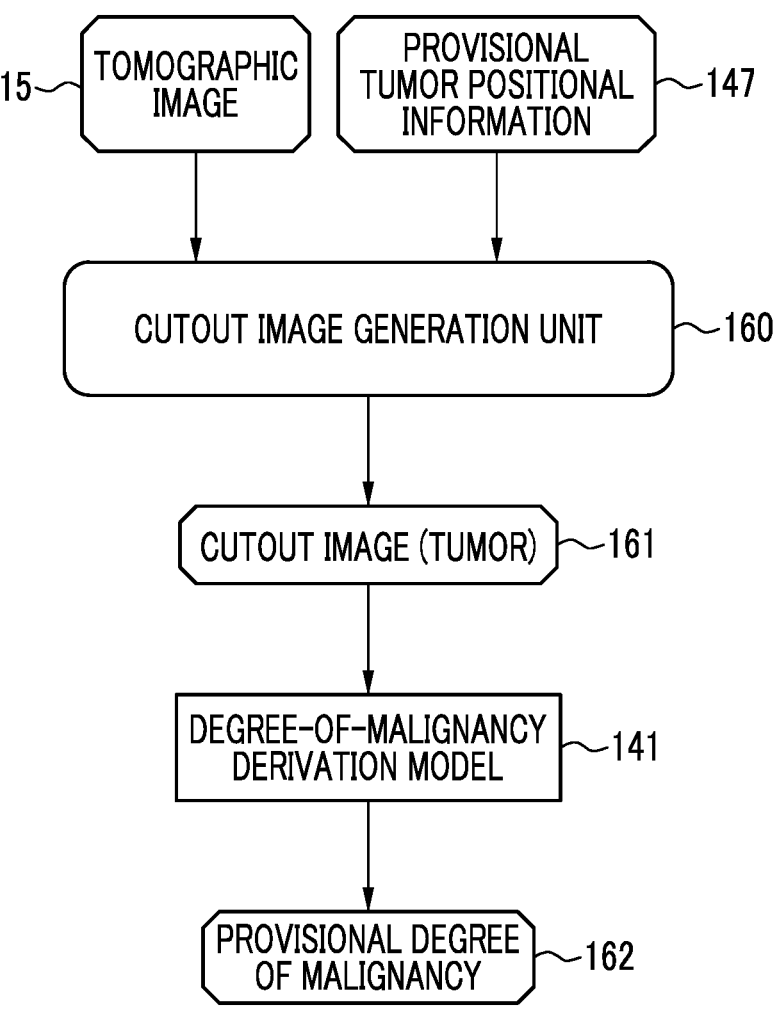
FIG. 22 is a diagram illustrating processing by a cutout image generation unit and a degree-of-malignancy derivation model of the second embodiment.

As an example, as illustrated in FIG. 22, the third derivation unit 135 includes a cutout image generation unit 160. The tomographic image 15 and the provisional tumor positional information 147 are input to the cutout image generation unit 160. The cutout image generation unit 160 generates a cutout image 161 in which a portion indicating a tumor is cut out in a box shape from the tomographic image 15 based on the provisional tumor positional information 147.

The third derivation unit 135 inputs the cutout image 161 to the degree-of-malignancy derivation model 141. Similar to the degree-of-malignancy derivation model 61, the degree-of-malignancy derivation model 141 is configured by the convolutional neural network. The degree-of-malignancy derivation model 141 derives a provisional degree of malignancy 162 of the tumor based on the cutout image 161. The provisional degree of malignancy 162 is, for example, 10 grades of 1 to 10, and the larger the value, the higher the probability that the tumor is malignant as in the degree of malignancy 92 of the first embodiment. The third derivation unit 135 outputs the provisional degree of malignancy 162 to the second derivation unit 44 or the like as the provisional lesion presence probability information 138.

Figure 23:
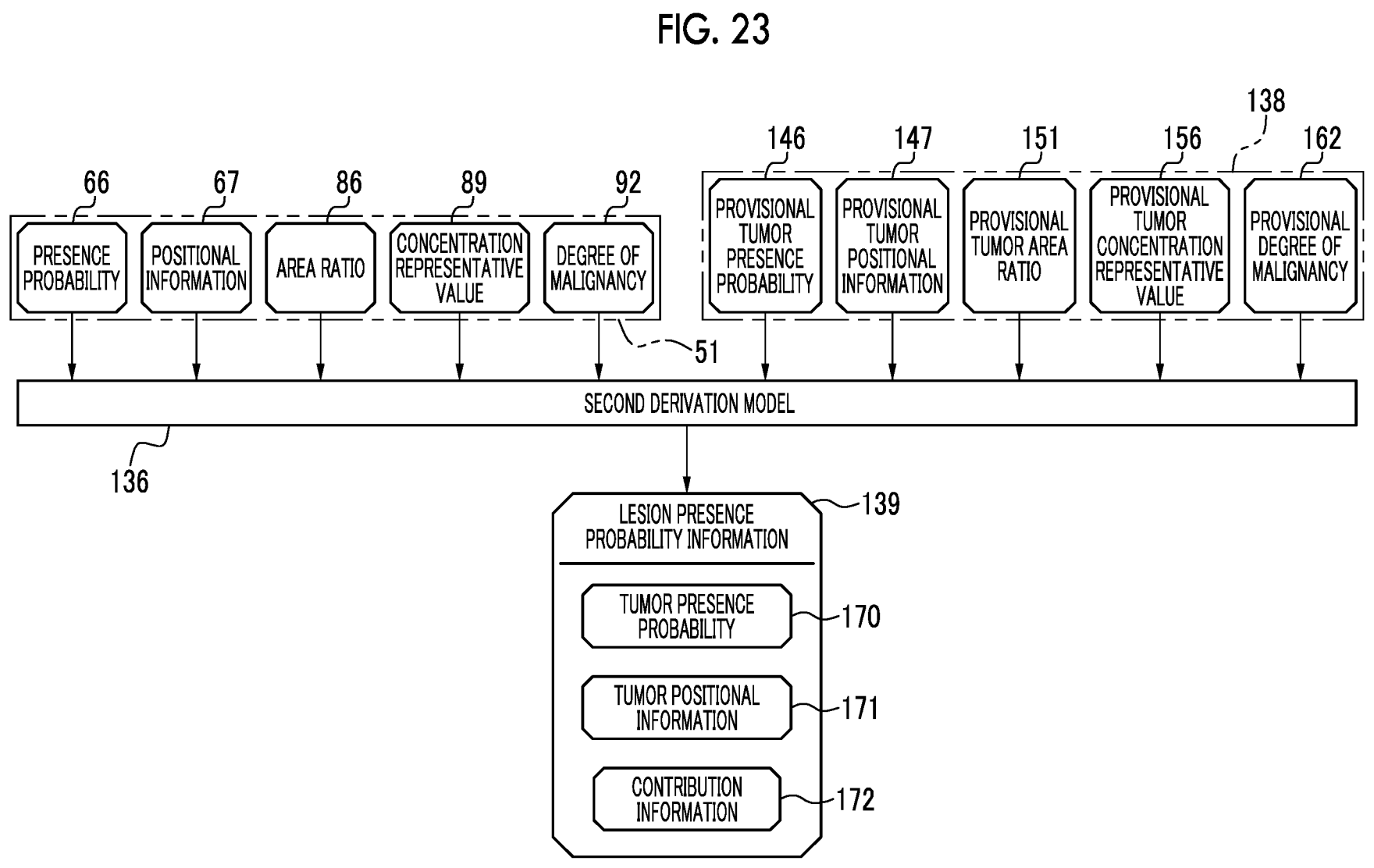

As an example, as illustrated in FIG. 23, the second derivation unit 44 inputs the indirect finding information 51 that is composed of the presence probability 66, the positional information 67, the area ratio 86, the concentration representative value 89, and the degree of malignancy 92 to the second derivation model 136. In addition, the second derivation unit 44 inputs the provisional lesion presence probability information 138, which is composed of the provisional tumor presence probability 146, the provisional tumor positional information 147, the provisional tumor area ratio 151, the provisional tumor concentration representative value 156, and the provisional degree of malignancy 162, to the second derivation model 136. The second derivation model 136 is constructed by, for example, a linear discriminant analysis method or a boosting method, similar to the second derivation model 33 of the first embodiment. The second derivation model 136 outputs the lesion presence probability information 139 based on the indirect finding information 51 and the provisional lesion presence probability information 138.

The lesion presence probability information 139 includes the tumor presence probability 170, the tumor positional information 171, and the contribution information 172, similar to the lesion presence probability information 52 of the first embodiment. As an example, as illustrated in FIG. 24, the contribution information 172 is information in which the contribution to the derivation of the tumor presence probability 170 and the tumor positional information 171 is registered for each indirect finding information 51 (the presence probability 66, the positional information 67, the area ratio 86, the concentration representative value 89, and the degree of malignancy 92) and for each provisional lesion presence probability information 138 (the provisional tumor presence probability 146, the provisional tumor positional information 147, the provisional tumor area ratio 151, the provisional tumor concentration representative value 156, and the provisional degree of malignancy 162).

Figure 25:
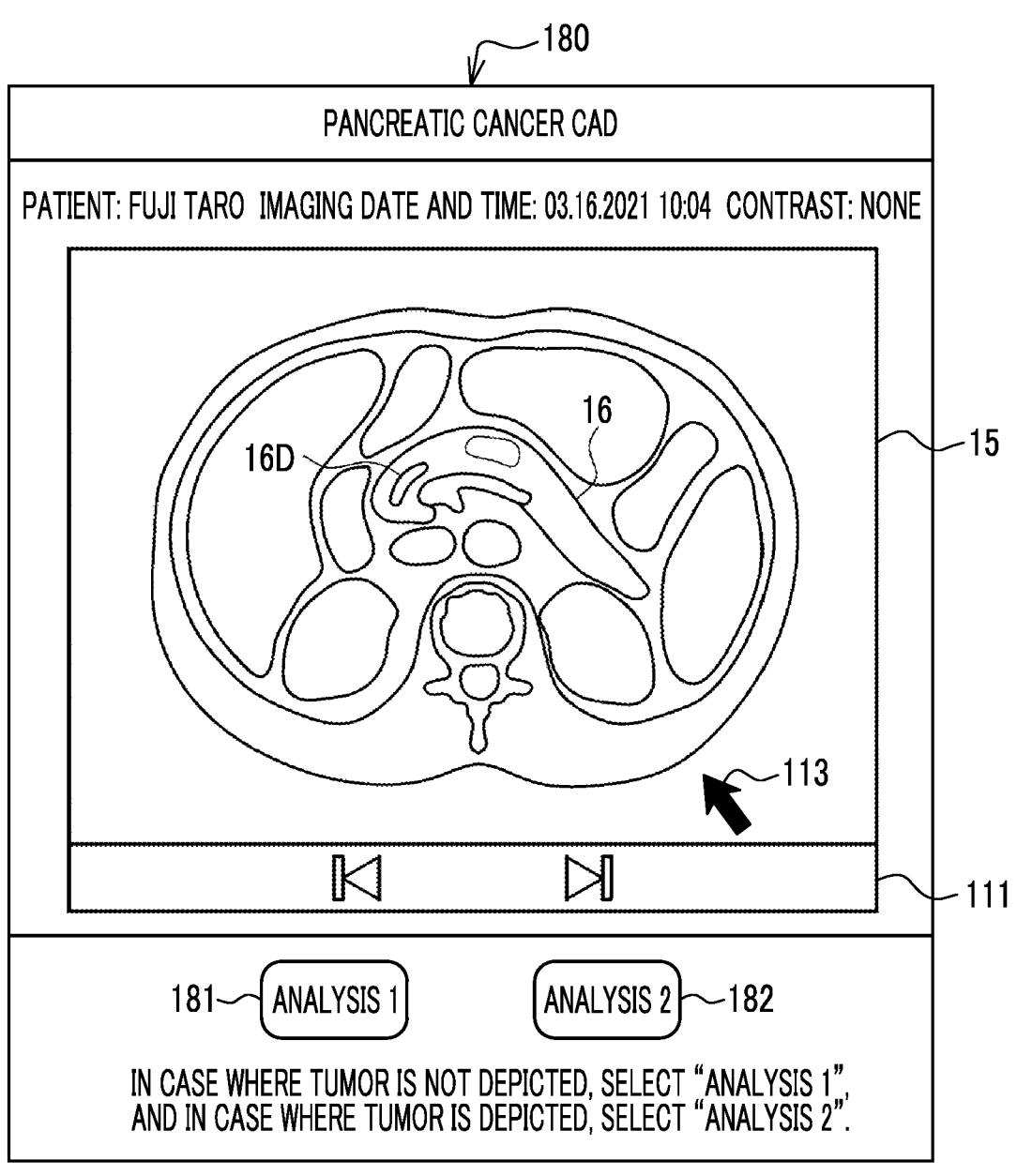
FIG. 25 is a diagram illustrating a first screen of the second embodiment.

As an example, as illustrated in FIG. 25, a first screen 180 of the second embodiment is provided with a first analysis button 181 and a second analysis button 182. In a case in which the doctor determines that the tumor is not depicted in the tomographic image 15, the doctor selects the first analysis button 181. On the other hand, in a case in which the doctor determines that the tumor is depicted in the tomographic image 15, the doctor selects the second analysis button 182.

In a case in which the first analysis button 181 is selected, a first analysis instruction for the tomographic image 15 is input to the instruction receiving unit 40. Accordingly, as in the case in which the analysis button 112 on the first screen 110 of the first embodiment is selected, the first derivation unit 43 and the second derivation unit 44 are operated, the indirect finding information 51 is derived by the first derivation unit 43, and the lesion presence probability information 52 is derived by the second derivation unit 44. In this case, the third derivation unit 135 is not operated.

On the other hand, in a case in which the second analysis button 182 is selected, a second analysis instruction of the tomographic image 15 is input to the instruction receiving unit 40. Accordingly, the first derivation unit 43, the second derivation unit 44, and the third derivation unit 135 are operated. Then, the indirect finding information 51 is derived by the first derivation unit 43, the provisional lesion presence probability information 138 is derived by the third derivation unit 135, and the lesion presence probability information 139 is derived by the second derivation unit 44.

Figure 26:
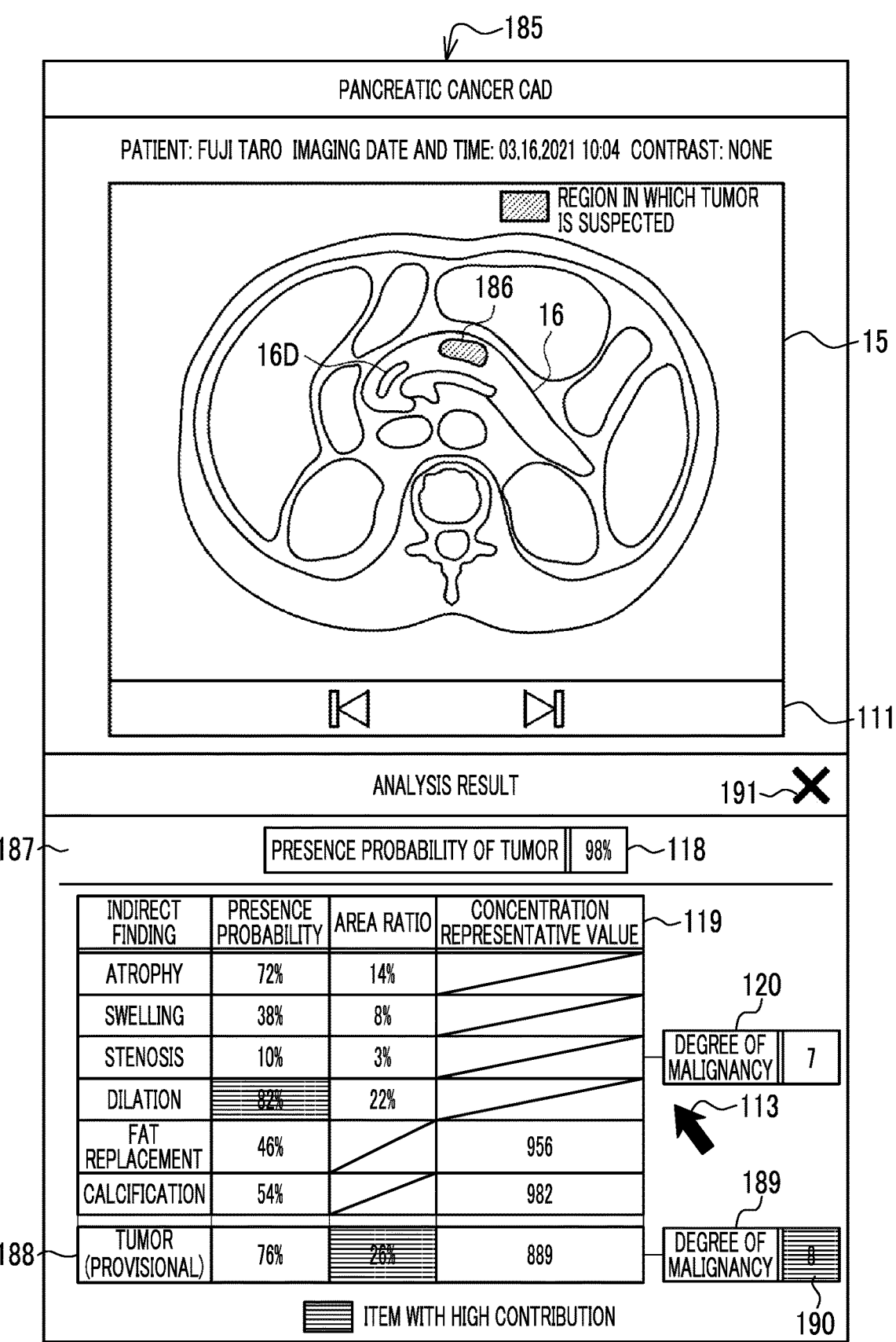
FIG. 26 is a diagram illustrating a second screen of the second embodiment.

After the second analysis button 182 is selected, the first screen 180 transitions to the second screen 185 illustrated in FIG. 26 as an example. On the tomographic image 15 of the second screen 185, a marker 186 indicating a region in which the tumor is suspected in the pancreas 16 is displayed based on the tumor positional information 171 of the lesion presence probability information 139. The marker 186 fills, for example, the pixel of the portion that seems to be a tumor registered in the tumor positional information 171 with red.

The second screen 185 has an analysis result display region 187 based on the indirect finding information 51, the provisional lesion presence probability information 138, and the lesion presence probability information 139 at the lower part of the second screen 185. In the analysis result display region 187, a display frame 118 of the tumor presence probability 170, a display frame 119 of the presence probability 66 of each indirect finding, the area ratio 86 of the shape indirect finding, and the concentration representative value 89 of the property indirect finding, and a display frame 120 of the degree of malignancy 92 are provided as in the analysis result display region 117 of the second screen 115 of the first embodiment. In addition, the analysis result display region 187 is provided with a display frame 188 for a provisional tumor presence probability 146, a provisional tumor area ratio 151, and a provisional tumor concentration representative value 156, and a display frame 189 for a provisional degree of malignancy 162. By displaying the second screen 185 on the display 17, the display control unit 45 presents the indirect finding information 51, the provisional lesion presence probability information 138, and the lesion presence probability information 139 to the doctor.

In the display frames 119, 120, 188, and 189, the display control unit 45 performs, for example, red hatching 190 on the indirect finding information 51 and the provisional lesion presence probability information 138, which have top three distributions registered in the contribution information 172. The display control unit 45 distinguishes the indirect finding information 51 and the provisional lesion presence probability information 138, which have the top three contributions to the derivation of the lesion presence probability information 139 as distinguished from the indirect finding information 51 and the provisional lesion presence probability information 138, which have a contribution lower than the third by the hatching 190. The indirect finding information 51 and the provisional lesion presence probability information 138, which have the top three contributions, are examples of "indirect finding information and the provisional lesion presence probability information, which have a relatively high contribution" according to the technology of the present disclosure. The indirect finding information 51 and the provisional lesion presence probability information 138, which have a contribution lower than the third, are examples of "indirect finding information and the provisional lesion presence probability information, which have a relatively low contribution" according to the technology of the present disclosure.

FIG. 26 illustrates a case in which the contributions of the presence probability 66 of the dilation, the provisional tumor area ratio 151, and the provisional degree of malignancy 162 are the top three. The display of the analysis result display region 187 disappears by selecting the close button 191. Accordingly, the second screen 185 returns to the first screen 180.

Figure 27:
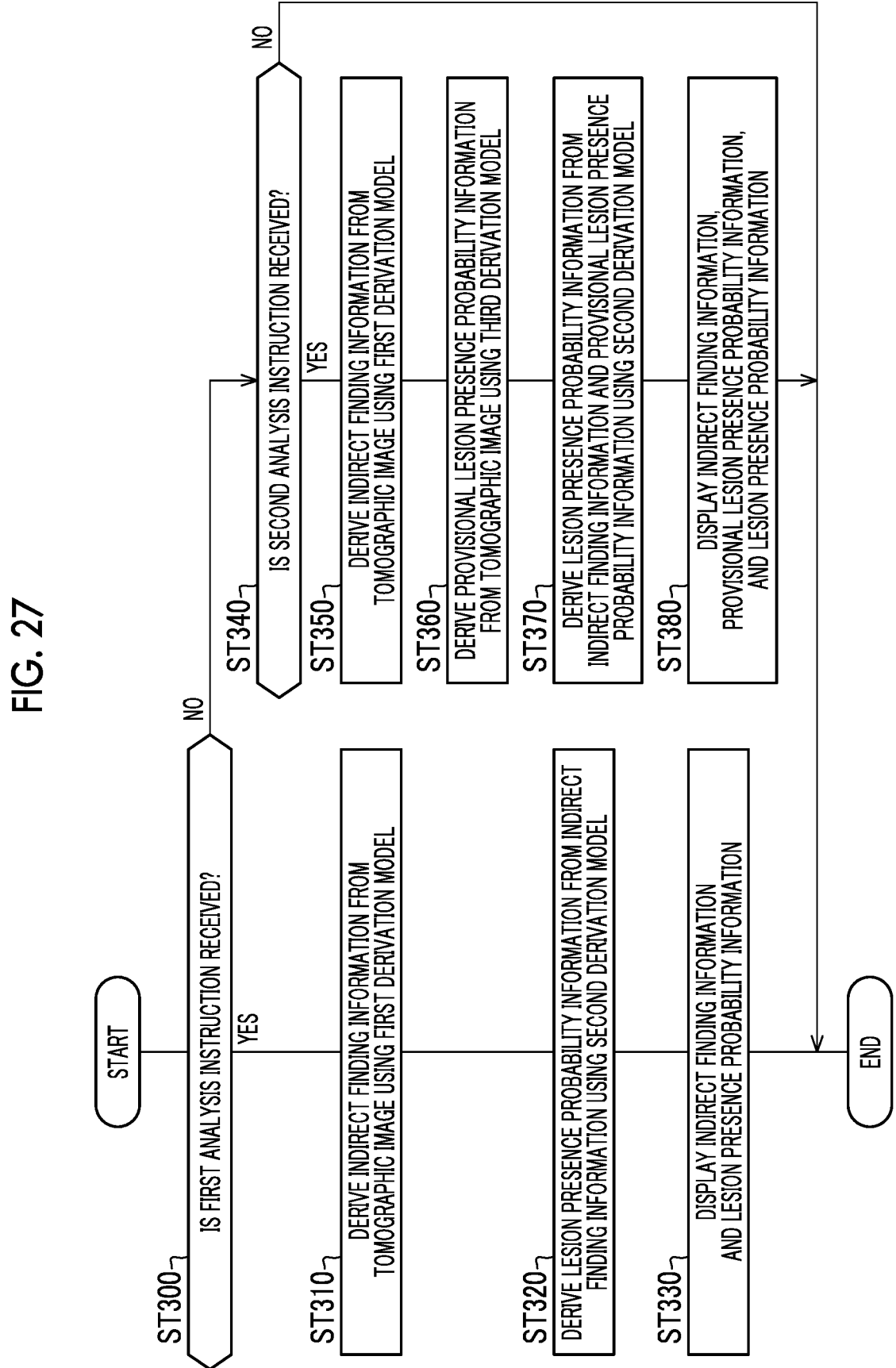
FIG. 27 is a flowchart illustrating a processing procedure of a doctor terminal of the second embodiment.

Next, an action of the above configuration will be described with reference to a flowchart shown in FIG. 27 as an example. Steps ST310 to ST330 in a case in which the first analysis button 181 of the first screen 180 is selected by the doctor and the first analysis instruction of the tomographic image 15 is received by the instruction receiving unit 40 (YES in Step ST300) are the same as Steps ST210 to ST230 illustrated in FIG. 16 in the first embodiment in a case in which the analysis button 112 is selected, and therefore the explanation is omitted.

In a case in which the second analysis button 182 of the first screen 180 is selected by the doctor and the second analysis instruction of the tomographic image 15 is received by the instruction receiving unit 40 (YES in Step ST340), the fact is output to the first derivation unit 43, the second derivation unit 44, and the third derivation unit 135. Then, the indirect finding information 51 is derived from the tomographic image 15 using the first derivation model 32 in the first derivation unit 43 (Step ST350). The indirect finding information 51 is output from the first derivation unit 43 to the second derivation unit 44 and the display control unit 45.

Next, as illustrated in FIGS. 19 to 22, in the third derivation unit 135, the provisional lesion presence probability information 138 is derived from the tomographic image 15 using the third derivation model 137 (Step ST360). The provisional lesion presence probability information 138 is output from the third derivation unit 135 to the second derivation unit 44.

Finally, as illustrated in FIG. 23, in the second derivation unit 44, the lesion presence probability information 139 is derived from the indirect finding information 51 and the provisional lesion presence probability information 138 using the second derivation model 136 (Step ST370). The lesion presence probability information 139 is output from the second derivation unit 44 to the display control unit 45.

As illustrated in FIG. 26, under the control of the display control unit 45, the second screen 185 including the analysis result display region 187 based on the indirect finding information 51, the provisional lesion presence probability information 138, and the lesion presence probability information 139 is displayed on the display 17 (Step ST380).

As described above, in the second embodiment, the third derivation unit 135 analyzes the tomographic image 15 to derive the provisional lesion presence probability information 138 indicating the provisional presence probability of the tumor. The second derivation unit 44 derives the lesion presence probability information 139 based on the indirect finding information 51 and the provisional lesion presence probability information 138. Therefore, in a case in which the tumor is visibly depicted in the tomographic image 15, the lesion presence probability information 139 can be derived by considering not only the indirect finding information 51 but also the provisional lesion presence probability information 138. Therefore, the reliability of the lesion presence probability information 139 can be improved.

As illustrated in FIG. 23, the provisional lesion presence probability information 138 includes the provisional tumor presence probability 146, the provisional tumor positional information 147, the provisional tumor area ratio 151, the provisional tumor concentration representative value 156, and the provisional degree of malignancy 162 of the tumor. Therefore, the features of the tumor can be expressed more succinctly.

As illustrated in FIG. 26, the display control unit 45 presents the indirect finding information 51 and the provisional lesion presence probability information 138 to the doctor. Therefore, the doctor can make a diagnosis of pancreatic cancer while referring not only to the tomographic image 15 but also to the indirect finding information 51 and the provisional lesion presence probability information 138. It is possible to reduce the burden on the doctor for diagnosis.

In addition, as illustrated in FIG. 26, the display control unit 45 presents, by the hatching 190, the indirect finding information 51 and the provisional lesion presence probability information 138, which have a relatively high contribution to the derivation of the lesion presence probability information 139 as distinguished from the indirect finding information 51 and the provisional lesion presence probability information 138, which have a relatively low contribution, to the doctor. Therefore, the doctor can see at a glance the indirect finding information 51 and the provisional lesion presence probability information 138, which have a relatively high contribution. The doctor can verify the validity of the lesion presence probability information 139.

Instead of or in addition to the provisional lesion presence probability information 138 of the tumor, the provisional lesion presence probability information of the cyst may be derived and the lesion presence probability information of the cyst may be derived based on the provisional lesion presence probability information of the cyst.

The indirect finding may represent at least one feature of a shape or a property of peripheral tissue of the lesion, which appears with the occurrence of the lesion. The indirect finding information 51 may be at least any one of the presence probability 66, the positional information 67, the area ratio 86, the concentration representative value 89, or the degree of malignancy 92. In addition, the provisional lesion presence probability information 138 may be at least any one of the provisional tumor presence probability 146, the provisional tumor positional information 147, the provisional tumor area ratio 151, the provisional tumor concentration representative value 156, or the provisional degree of malignancy 162.

The lesion presence probability information 52 (139) may be at least any one of the tumor presence probability 100 (170) or the tumor positional information 101 (171). Similarly, the lesion presence probability information 126 may be at least any one of the cyst presence probability 127 or the cyst positional information 128.

The shape indirect finding may be at least any one of atrophy, swelling, stenosis, or dilation. In addition, the property indirect finding may be at least any one of fat replacement or calcification.

The portion of the tomographic image 15 which is emphasized when the SS model 60 outputs the output image 65 may be displayed separately from the others. Similarly, the portion of the tomographic image 15 which is emphasized when the SS model 140 outputs the output image 145 may be displayed separately from the others.

The presence probability 66 is derived from the probability distribution map 78, but the present disclosure is not limited to this. A machine learning model outputs the presence probability 66 when the tomographic image 15 is input may be used.

The method of deriving the lesion presence probability information 52 from the indirect finding information 51 is not limited to the method of using the second derivation model 33. A rule base in which the lesion presence probability information 52 corresponding to various types of patterns of the indirect finding information 51 is registered may be used. The same applies to a case in which the lesion presence probability information 139 is derived from the indirect finding information 51 and the provisional lesion presence probability information 138.

The shape feature amount of the indirect finding is not limited to the exemplified area ratio 86. Instead of or in addition to the area ratio 86, the shape feature amount of the indirect finding may be the ratio of atrophy or swelling of pancreatic head, pancreatic body, and pancreatic tail, the diameter of the pancreatic duct 16D where stenosis or dilation is seen, the area of the portion indicating fat replacement, the area of the portion indicating calcification, or the like. The property feature amount of the indirect finding is not limited to the exemplified concentration representative value 89. Instead of or in addition to the concentration representative value 89, the property feature amount of the indirect finding may be the dispersion of the distribution of the pixel value of the pixels of the portion indicating fat replacement, the dispersion of the distribution of the pixel values of the pixels of the portion indicating calcification, the graininess of the portion indicating calcification, or the like. The feature amount map 72 and/or the final feature amount map 77 of the SS model 60 may be used as the shape feature amount of the indirect finding and the property feature amount of the indirect finding.

The provisional shape feature amount of the lesion is not limited to the exemplified provisional tumor area ratio 151. Instead of or in addition to the provisional tumor area ratio 151, the size, circularity, sharpness, or the like of a portion indicating a tumor may be used. The provisional property feature amount of the lesion is also not limited to the exemplified provisional tumor concentration representative value 156. Instead of, or in addition to, the provisional tumor concentration representative value 156, the dispersion of the distribution of pixel values of the portion indicating the tumor, graininess of the portion indicating the tumor, or the like may be used. The feature amount map and/or the final feature amount map of the SS model 140 may be used as the provisional shape feature amount of the lesion and the provisional property feature amount of the lesion.

The method of displaying the indirect finding information 51 having a relatively high contribution to the derivation of the lesion presence probability information 52 as distinguished from the indirect finding information 51 having a relatively low contribution is not limited to the exemplified hatching 121. The color of the numerical values of the indirect finding information 51 having a relatively high contribution may be different from the color of the numerical values of the indirect finding information 51 having a relatively low contribution. For example, the former color is red and the latter color is black. Alternatively, the numerical value of the indirect finding information 51 having a relatively high contribution may be bolded. Alternatively, only the indirect finding information 51 having a relatively high contribution may be displayed. The method of displaying the indirect finding information 51 and the provisional lesion presence probability information 138, which have a relatively high contribution to the derivation of the lesion presence probability information 139 as distinguished from the indirect finding information 51 and the provisional lesion presence probability information 138, which have a relatively low contribution is the same.

The indirect finding information 51, the provisional lesion presence probability information 138, and the lesion presence probability information 52, 126, and 139 may be stored in the storage 20.

Instead of the SS model 60, a machine learning model that detects a box-shaped region surrounding a portion indicating the indirect finding may be used. Similarly, instead of the SS model 140, a machine learning model that detects a box-shaped region surrounding a portion indicating the tumor may be used.

The medical image is not limited to the non-contrast tomographic image of the abdomen on which the pancreas is shown. A contrast tomographic image of the abdomen showing the pancreas may also be used. In addition, a tomographic image of the head or a tomographic image of the chest may also be used. The disease to be diagnosed by the doctor is not limited to the exemplified pancreatic cancer. The disease may be pancreatitis. In addition, it may be esophageal cancer, gastric cancer, gastritis, lung cancer, pulmonary edema, liver cancer, hepatitis, colon cancer, and the like.

The medical image is not limited to the tomographic image 15 captured by the CT device 10. For example, a tomographic image captured by a magnetic resonance imaging (MRI) device may be used. In addition, the medical image is not limited to a three-dimensional image such as a tomographic image. For example, a two-dimensional image such as a simple radiation image may be used. The medical image may be a positron emission tomography (PET) image, a single photon emission computed tomography (SPECT) image, an endoscopic image, an ultrasound image, or the like.

The form of presenting the lesion presence probability information 52 or the like to the doctor is not limited to the form of displaying the exemplified second screen 115 or the like on the display 17. The lesion presence probability information 52 or the like may be printed on a paper medium, or the lesion presence probability information 52 or the like may be attached to an e-mail and sent to the doctor terminal 12.

Various modifications may be made to the hardware configuration of the computer that configures the medical image processing device of the present disclosure. For example, the medical image processing device may be configured by a plurality of computers which are separated as hardware for the purpose of improving processing capability and reliability. For example, the functions of the instruction receiving unit 40, the image acquisition unit 41, the RW control unit 42, and the display control unit 45 and the functions of the first derivation unit 43 and the second derivation unit 44 are carried by two computers in a distributed manner. In this case, the medical image processing device is configured by two computers.

In addition, the function of the medical image processing device may be carried by the PACS server 11 or another server instead of the doctor terminal 12. In this case, the PACS server 11 or another server distributes various types of screens such as the first screen 110 to the doctor terminal 12 in a format of screen data for web distribution created by a markup language such as an extensible markup language (XML). The doctor terminal 12 reproduces various types of screens to be displayed on the web browser based on the screen data and displays the screens on the display 17. Instead of XML, another data description language such as JavaScript (registered trademark) object notation (JSON) may be used.

The PACS server 11 or another server receives a request from the doctor terminal 12 to analyze the tomographic image 15. The PACS server 11 or another server derives the indirect finding information 51 from the tomographic image 15, and derives the lesion presence probability information 52 from the indirect finding information 51. The PACS server 11 or another server generates the screen data of the second screen 115 and distributes the screen data to the doctor terminal 12.

As described above, the hardware configuration of the computer of the medical image processing device can be appropriately changed according to the required performance such as processing capacity, safety, and reliability. Further, it is needless to say that, in addition to the hardware, an application program, such as the operation program 30, can be duplicated or distributed and stored in a plurality of storages for the purpose of securing the safety and the reliability.

In each of the embodiments, for example, as a hardware structure of the processing unit that executes various types of processing, such as the instruction receiving unit 40, the image acquisition unit 41, the RW control unit 42, the first derivation unit 43, the second derivation unit 44, the display control unit 45, the shape feature amount derivation units 85 and 150, the property feature amount derivation units 88 and 155, the cutout image generation units 90 and 160, and the third derivation unit 135, the following various types of processors may be used. As described above, the various types of processors include, in addition to the CPU 22 that is a general-purpose processor which executes software (the operation program 30) to function as various processing units, a programmable logic device (PLD) that is a processor of which a circuit configuration can be changed after manufacture, such as a field programmable gate array (FPGA), and a dedicated electrical circuit that is a processor having a circuit configuration which is designed for exclusive use to execute a specific processing, such as an application specific integrated circuit (ASIC).

One processing unit may be formed of one of these various processors, or may be formed of a combination of two or more processors of the same type or different types (for example, a combination of a plurality of FPGAs and/or a combination of a CPU and an FPGA). In addition, a plurality of processing units may be formed of one processor.

Examples of the plurality of processing units composed of one processor include, first, as represented by a computer such as a client and a server, a form in which one processor is composed of a combination of one or more CPUs and software, and the processor functions as the plurality of processing units. Second, there is an aspect where a processor realizing the functions of the entire system, which includes a plurality of processing units, by one integrated circuit (IC) chip as typified by System On Chip (SoC) or the like is used. In this way, various types of processing units are formed using one or more of the above-mentioned various processors as hardware structures.

Furthermore, specifically, an electric circuit (circuitry) obtained by combining circuit elements, such as semiconductor elements, can be used as the hardware structure of the various processors.

In the technology of the present disclosure, the above-described various embodiments and/or various modification examples may be combined with each other as appropriate. In addition, the present disclosure is not limited to each of the above-described embodiments, and various configurations can be used without departing from the gist of the present disclosure.

The above descriptions and illustrations are detailed descriptions of portions related to the technology of the present disclosure and are merely examples of the technology of the present disclosure. For example, description related to the above configurations, functions, actions, and effects is description related to an example of configurations, functions, actions, and effects of the parts according to the technology of the present disclosure. Therefore, unnecessary portions may be deleted or new elements may be added or replaced in the above descriptions and illustrations without departing from the gist of the technology of the present disclosure. Further, in order to avoid complications and facilitate understanding of the parts related to the technology of the present disclosure, descriptions of common general knowledge and the like that do not require special descriptions for enabling the implementation of the technology of the present disclosure are omitted, in the contents described and illustrated above.

In the present specification, the term "A and/or B" is synonymous with the term "at least one of A or B". That is, the term "A and/or B" means only A, only B, or a combination of A and B. In addition, in the present specification, the same approach as "A and/or B" is applied to a case in which three or more matters are represented by connecting the matters with "and/or".

All documents, patent applications, and technical standards disclosed in this specification are incorporated in this specification by reference such that the incorporation of each of the documents, the patent applications, and the technical standards by reference is specific and is as detailed as that in a case where the documents, the patent applications, and the technical standards are described individually.

What is claimed is:

1. A medical image processing device comprising:
a processor; and
a memory connected to or built in the processor,
wherein the processor is configured to:
acquire a medical image;
derive indirect finding information related to an indirect finding that represents at least one feature of a shape or a property of peripheral tissue of a lesion associated with an occurrence of the lesion by analyzing the medical image using a first derivation model; and
derive lesion presence probability information that indicates a presence probability of the lesion based on the indirect finding information using a second derivation model,
wherein the first derivation model and the second derivation model are machine learning models,
wherein the indirect finding that represents the feature of the shape includes at least one of atrophy, swelling, stenosis, or dilation, and
wherein the indirect finding that represents the feature of the property includes at least one of fat replacement or calcification.

2. The medical image processing device according to claim 1,
wherein the indirect finding information is at least one of a presence probability of the indirect finding, positional information of the indirect finding, a shape feature amount of the indirect finding, a property feature amount of the indirect finding, a property feature amount of the indirect finding, or a degree of malignancy of the lesion based on the indirect finding.

3. The medical image processing device according to claim 1,
wherein the lesion presence probability information is at least one of a presence probability of the lesion or positional information of the lesion.

4. The medical image processing device according to claim 1,
wherein the processor is configured to present the lesion presence probability information.

5. The medical image processing device according to claim 1,
wherein the processor is configured to present the indirect finding information.

6. The medical image processing device according to claim 5,
wherein the processor is configured to present the indirect finding information having a relatively high contribution to the derivation of the lesion presence probability information as distinguished from the indirect finding information having a relatively low contribution.

7. The medical image processing device according to claim 1,
wherein the processor is configured to:
derive provisional lesion presence probability information that indicates a provisional presence probability of the lesion, which represents at least one feature of a shape or a property of the lesion, by analyzing the medical image; and
derive the lesion presence probability information based on the indirect finding information and the provisional lesion presence probability information.

8. The medical image processing device according to claim 7,
wherein the provisional lesion presence probability information is at least one of a provisional presence probability of the lesion, provisional positional information of the lesion, a provisional shape feature amount of the lesion, a provisional property feature amount of the lesion, or a provisional degree of malignancy of the lesion.

9. The medical image processing device according to claim 7,
wherein the processor is configured to present the indirect finding information and the provisional lesion presence probability information.

10. The medical image processing device according to claim 9,
wherein the processor is configured to present the indirect finding information and the provisional lesion presence probability information, which have a relatively high contribution to the derivation of the lesion presence probability information as distinguished from the indirect finding information and the provisional lesion presence probability information, which have a relatively low contribution.

11. The medical image processing device according to claim 1,
wherein the lesion includes at least one of a tumor or a cyst.

12. The medical image processing device according to claim 1,
wherein the medical image is a non-contrast tomographic image of an abdomen in which a pancreas is shown and is used for diagnosing pancreatic cancer.

13. An operation method of a medical image processing device, comprising:

acquiring a medical image;

deriving indirect finding information related to an indirect finding that represents at least one feature of a shape or a property of peripheral tissue of a lesion associated with an occurrence of the lesion by analyzing the medical image using a first derivation model; and deriving lesion presence probability information that indicates a presence probability of the lesion based on the indirect finding information using a second derivation model, wherein the first derivation model and the second derivation model are machine learning models, wherein the indirect finding that represents the feature of the shape includes at least one of atrophy, swelling, stenosis, or dilation, and wherein the indirect finding that represents the feature of the property includes at least one of fat replacement or calcification.

14. A non-transitory computer-readable storage medium storing an operation program of a medical image processing device for causing a computer to execute a process comprising:

acquiring a medical image;

deriving indirect finding information related to an indirect finding that represents at least one feature of a shape or a property of peripheral tissue of a lesion associated with an occurrence of the lesion by analyzing the medical image using a first derivation model; and deriving lesion presence probability information that indicates a presence probability of the lesion based on the indirect finding information using a second derivation model, wherein the first derivation model and the second derivation model are machine learning models, wherein the indirect finding that represents the feature of the shape includes at least one of atrophy, swelling, stenosis, or dilation, and wherein the indirect finding that represents the feature of the property includes at least one of fat replacement or calcification.

* * * * *